(12) United States Patent
Re et al.

(10) Patent No.: US 8,292,897 B2
(45) Date of Patent: *Oct. 23, 2012

(54) APPARATUS AND METHOD FOR RECONSTRUCTING A LIGAMENT

(75) Inventors: Paul Re, Lexington, MA (US); Mark A. Johanson, Littleton, MA (US); Peter F. Marshall, Lancaster, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/964,817

(22) Filed: Dec. 10, 2010

(65) Prior Publication Data

US 2011/0144650 A1   Jun. 16, 2011

Related U.S. Application Data

(63) Continuation of application No. 11/454,659, filed on Jun. 16, 2006, now Pat. No. 7,862,612, which is a continuation of application No. 10/793,532, filed on Mar. 4, 2004, now Pat. No. 7,063,724, which is a continuation of application No. 10/123,434, filed on Apr. 16, 2002, now Pat. No. 6,712,849.

(60) Provisional application No. 60/326,351, filed on Oct. 1, 2001.

(51) Int. Cl.
*A61B 17/58* (2006.01)
*A61F 2/08* (2006.01)

(52) U.S. Cl. ............................ 606/99; 606/98; 623/13.14

(58) Field of Classification Search .................... 606/96, 606/98, 99; 623/13.14
See application file for complete search history.

(56) References Cited

U.S. PATENT DOCUMENTS

| | | | |
|---|---|---|---|
| 3,973,277 | A | 8/1976 | Semple et al. |
| 5,147,362 | A | 9/1992 | Goble |
| 5,234,430 | A | 8/1993 | Huebner |
| 5,324,308 | A | 6/1994 | Pierce |
| 5,356,413 | A | 10/1994 | Martins et al. |
| 5,397,356 | A | 3/1995 | Goble et al. |
| 5,464,427 | A | 11/1995 | Curtis et al. |
| 5,505,735 | A | 4/1996 | Li |
| 5,507,812 | A | 4/1996 | Moore |

(Continued)

FOREIGN PATENT DOCUMENTS

DE        4127550 A1     2/1993

(Continued)

OTHER PUBLICATIONS

European Search Report for corresponding EP 02766415 mailing is Dec. 18, 2009 (3 pages).

*Primary Examiner* — Bruce E Snow

(57) ABSTRACT

A system for installation of a graft ligament support block is provided. The system includes an installation tool having a holder including a shaft having a handle at a proximal end and a distal end configured for selectively engaging the graft ligament support block. The installation tool further includes a drill guide including an outrigger having a bore formed on its distal end for selectively receiving a drill sleeve and a proximal end configured to selectively engage the holder. Also provided is a kit for use in reconstructing a ligament. The kit includes an installation tool including a holder and a drill guide, a drill sleeve, a guidewire, one or more drills, one or more graft ligament support blocks and one or more transverse fixation pins.

16 Claims, 42 Drawing Sheets

U.S. PATENT DOCUMENTS

| | | |
|---|---|---|
| 5,545,180 A | 8/1996 | Le et al. |
| 5,562,671 A | 10/1996 | Goble et al. |
| 5,578,044 A | 11/1996 | Gordon et al. |
| 5,601,562 A * | 2/1997 | Wolf et al. ............... 606/86 R |
| 5,618,314 A | 4/1997 | Harwin et al. |
| 5,632,748 A | 5/1997 | Beck, Jr. et al. |
| 5,690,676 A | 11/1997 | DiPoto et al. |
| 5,702,397 A | 12/1997 | Goble et al. |
| 5,713,910 A | 2/1998 | Gordon et al. |
| 5,849,013 A | 12/1998 | Whittaker et al. |
| 5,931,869 A | 8/1999 | Boucher et al. |
| 5,961,520 A | 10/1999 | Beck, Jr. et al. |
| 5,989,253 A | 11/1999 | Bigliardi |
| 5,993,486 A | 11/1999 | Tomatsu |
| 6,001,100 A | 12/1999 | Sherman et al. |
| 6,066,173 A | 5/2000 | McKernan et al. |
| 6,113,604 A | 9/2000 | Whittaker et al. |
| 6,132,433 A | 10/2000 | Whelan |
| 6,214,007 B1 | 4/2001 | Anderson |
| 6,264,694 B1 | 7/2001 | Weiler |
| 6,325,804 B1 | 12/2001 | Wenstrom, Jr. et al. |
| 6,355,066 B1 | 3/2002 | Kim |
| 6,387,129 B2 | 5/2002 | Rieser et al. |
| 6,440,134 B1 | 8/2002 | Zaccherotti et al. |
| 6,712,849 B2 | 3/2004 | Re et al. |
| 7,063,724 B2 | 6/2006 | Re et al. |
| 7,520,898 B2 | 4/2009 | Re et al. |
| 2004/0127988 A1 | 7/2004 | Goble et al. |
| 2005/0033301 A1 | 2/2005 | Lombardo et al. |

FOREIGN PATENT DOCUMENTS

| | | |
|---|---|---|
| EP | 1072234 A2 | 1/2001 |
| WO | WO94/28799 A1 | 12/1994 |
| WO | WO 99/59488 | 11/1999 |

* cited by examiner

APPARATUS AND METHOD FOR RECONSTRUCTING A LIGAMENT

CROSS REFERENCE TO RELATED APPLICATIONS

The present application is a Continuation of U.S. Ser. No. 11/454,659, filed Jun. 16, 2006 now U.S. Pat. No. 7,862,612, which is a Continuation of U.S. Ser. No. 10/793,532, filed Mar. 4, 2004, now U.S. Pat. No. 7,063,724, which is a Continuation of Ser. No. 10/123,434, filed Apr. 16, 2002, now U.S. Pat. 6,712,849, which claims the benefit of and priority to U.S. Provisional Application Ser. No. 60/326,351, filed Oct. 1, 2001. The entire contents of each of these applications are incorporated herein by reference.

FIELD OF THE INVENTION

This invention relates to surgical apparatus and procedures in general, and more particularly to surgical apparatus and procedures for reconstructing a ligament.

BACKGROUND OF THE INVENTION

A ligament is a piece of fibrous tissue which connects one bone to another.

Ligaments are frequently damaged (e.g., detached or torn or ruptured, etc.) as the result of injury and/or accident. A damaged ligament can cause instability, impede proper motion of a joint and cause pain.

Various procedures have been developed to repair or replace a damaged ligament. The specific procedure used depends on the particular ligament which is to be restored and on the extent of the damage.

One ligament which is frequently damaged as the result of injury and/or accident is the anterior cruciate ligament (i.e., the ACL). Looking first at FIGS. 1 and 2, it will be seen that the ACL 5 extends between the top of the tibia 10 and the bottom of the femur 15. A damaged ACL can cause instability of the knee joint and cause substantial pain and arthritis.

Numerous procedures have been developed to restore a damaged ACL through a graft ligament replacement. In general, and looking next at FIG. 3, these ACL replacement procedures involve drilling a bone tunnel 20 up through tibia 10 and drilling a bone tunnel 25 up into femur 15. In some cases the femoral tunnel 25 may be in the form of a blind hole and terminate in a distal end surface 30; in other cases the femoral tunnel 25, or an extension of the femoral tunnel 25, may pass completely through femur 15. Once tibial tunnel 20 and femoral tunnel 25 have been formed, a graft ligament 35, consisting of a harvested or artificial ligament or tendon(s), is passed up through tibial tunnel 20, across the interior of the knee joint, and up into femoral tunnel 25. Then a distal portion of graft ligament 35 is secured in femoral tunnel 25 and a proximal portion of graft ligament 35 is secured in tibial tunnel 20.

There are currently a number of different ways to secure a graft ligament in a bone tunnel. One way is to use an interference screw 40 (FIG. 4) to wedge the graft ligament against an opposing side wall of the bone tunnel. Another way is to suspend the graft ligament in the bone tunnel with a button 45 and a suture 50 (FIG. 5) or with a crosspin 55 (FIG. 6). Still another way is to pass the graft ligament completely through the bone tunnel and affix the graft ligament to the outside of the bone with a screw 60 and washer 65 (FIG. 7) or with a staple (not shown).

The "Gold Standard" of ACL repair is generally considered to be the so-called "Bone-Tendon-Bone" fixation. In this procedure, a graft of the patella tendon is used to replace the natural ACL. Attached to the opposing ends of the harvested tendon are bone grafts, one taken from the patient's knee cap (i.e., the patella) and one taken from the patient's tibia (i.e., at the location where the patella tendon normally attaches to the tibia). The graft ligament is then deployed in the bone tunnels, with one bone graft being secured in the femoral tunnel with an interference screw and the other bone graft being secured in the tibial tunnel with another interference screw. Over the years, this procedure has generally yielded a consistent, strong and reliable ligament repair. However, this procedure is also generally considered to be highly invasive and, in many cases, quite painful, and typically leaves unsightly scarring on the knee and a substantial void in the knee cap.

As a result, alternative procedures have recently been developed that incorporate the use of soft tissue grafts such as the hamstring tendon. However, soft tissue grafts such as the hamstring can be difficult to stabilize within a bone tunnel. More particularly, the use of an interference screw to aggressively wedge the hamstring against an opposing side wall of the bone tunnel can introduce issues such as graft slippage, tendon winding, tissue necrosis and tendon cutting. Furthermore, the use of a suture sling (e.g., such as that shown in FIG. 5) and/or a crosspin (e.g., such as that shown in FIG. 6) to suspend the hamstring within the bone tunnel can introduce a different set of issues, e.g., it has been found that the suture sling and/or crosspin tend to permit the graft ligament to move laterally within the bone tunnel, with a so-called "windshield wiper" effect, thereby impeding ingrowth between the graft ligament and the host bone and/or causing abrasion and/or other damage to the graft tissue. In addition, the use of a crosspin (e.g., such as that shown in FIG. 6) to secure a hamstring within the bone tunnel can introduce still other issues, e.g., difficulties in looping the hamstring over the crosspin, or tearing of the hamstring along its length during tensioning if and where the crosspin passes through the body of the hamstring, etc.

SUMMARY OF THE INVENTION

As a result, one object of the present invention is to provide improved apparatus for reconstructing a ligament, wherein the apparatus is adapted to permit the graft ligament to be fashioned out of various soft tissue grafts, e.g., allografts, autografts, xenografts, bioengineered tissue grafts or synthetic grafts, and further wherein the graft is intended to be secured in place using a transverse fixation pin.

Another object of the present invention is to provide an improved method for reconstructing a ligament, wherein the method is adapted to permit the graft ligament to be fashioned out of various soft tissue grafts, e.g., allografts, autografts, xenografts, bioengineered tissue grafts or synthetic grafts, and further wherein the graft is intended to be secured in place using a transverse fixation pin.

These and other objects are addressed by the present invention which comprises, in one preferred form of the invention, the provision and use of a graft ligament support block which comprises a body, and a graft hole and a transverse fixation pin hole extending through the body, with both the graft hole and the transverse fixation pin hole preferably extending substantially perpendicular to the longitudinal axis of the body. In one preferred form of the invention, the invention also comprises an installation tool for inserting the graft ligament support block into the bone tunnel and, while supporting the graft ligament support block in the bone tunnel, forming a transverse tunnel in the host bone, with the transverse tunnel in the host bone being aligned with the transverse fixation pin hole in the graft ligament support block.

In one preferred method of use, a graft ligament is looped through the graft hole in the graft ligament support block, and the graft ligament support block is mounted to the installation tool. The two free ends of the graft ligament are then preferably secured to a proximal portion of the installation tool under tension, whereby to tie down the two free ends of the graft ligament. In addition to controlling the two free ends of the graft ligament, this arrangement will also help hold the graft ligament support block to the installation tool. Then the installation tool is used to advance the graft ligament support block through the tibial tunnel, across the interior of the knee joint, and up into the femoral tunnel, with the two free ends of the looped graft ligament extending back out through the tibial tunnel. Next, a transverse tunnel is formed in the host bone, with the transverse tunnel being aligned with the transverse fixation pin hole in the graft ligament support block. Then the graft ligament support block is secured in place by pinning the graft ligament support block within the femoral tunnel, i.e., by advancing a transverse fixation pin along the transverse tunnel in the host bone and into the transverse fixation pin hole in the graft ligament support block. Then the two free ends of the looped graft ligament are released from the installation tool, the installation tool is detached from the graft ligament support block, and the installation tool is withdrawn from the surgical site. Finally, the two free ends of the looped graft ligament are secured to the tibia, thus completing the ACL repair. If desired, the tibial attachment can be effected using a second graft ligament support block.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENT

Figure 1:
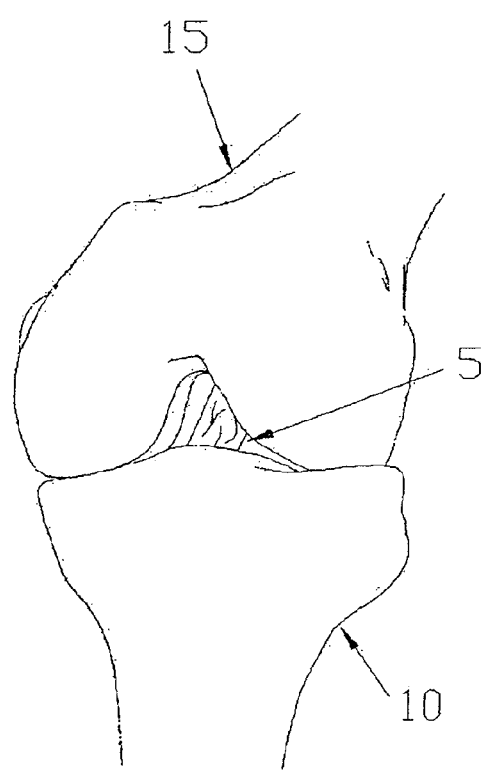
FIG. 1 is a schematic view of a knee joint, as viewed from the anterior side.
Figure 2:
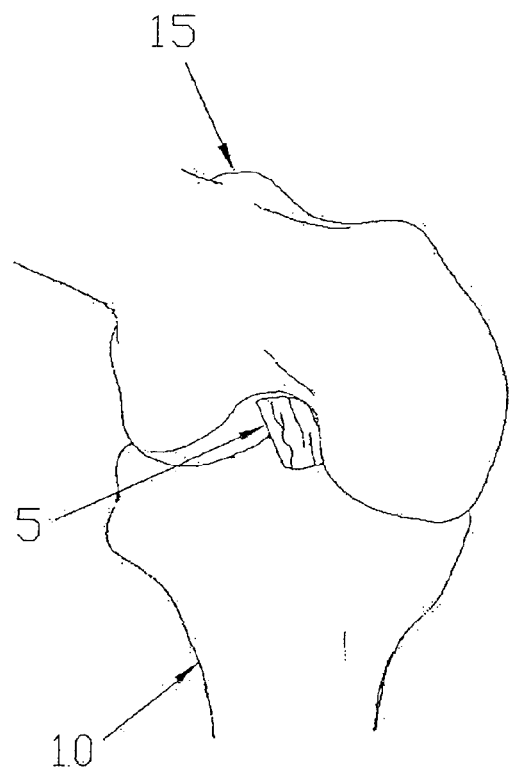
FIG. 2 is a schematic view of a knee joint, as viewed from the posterior side.
Figure 3:
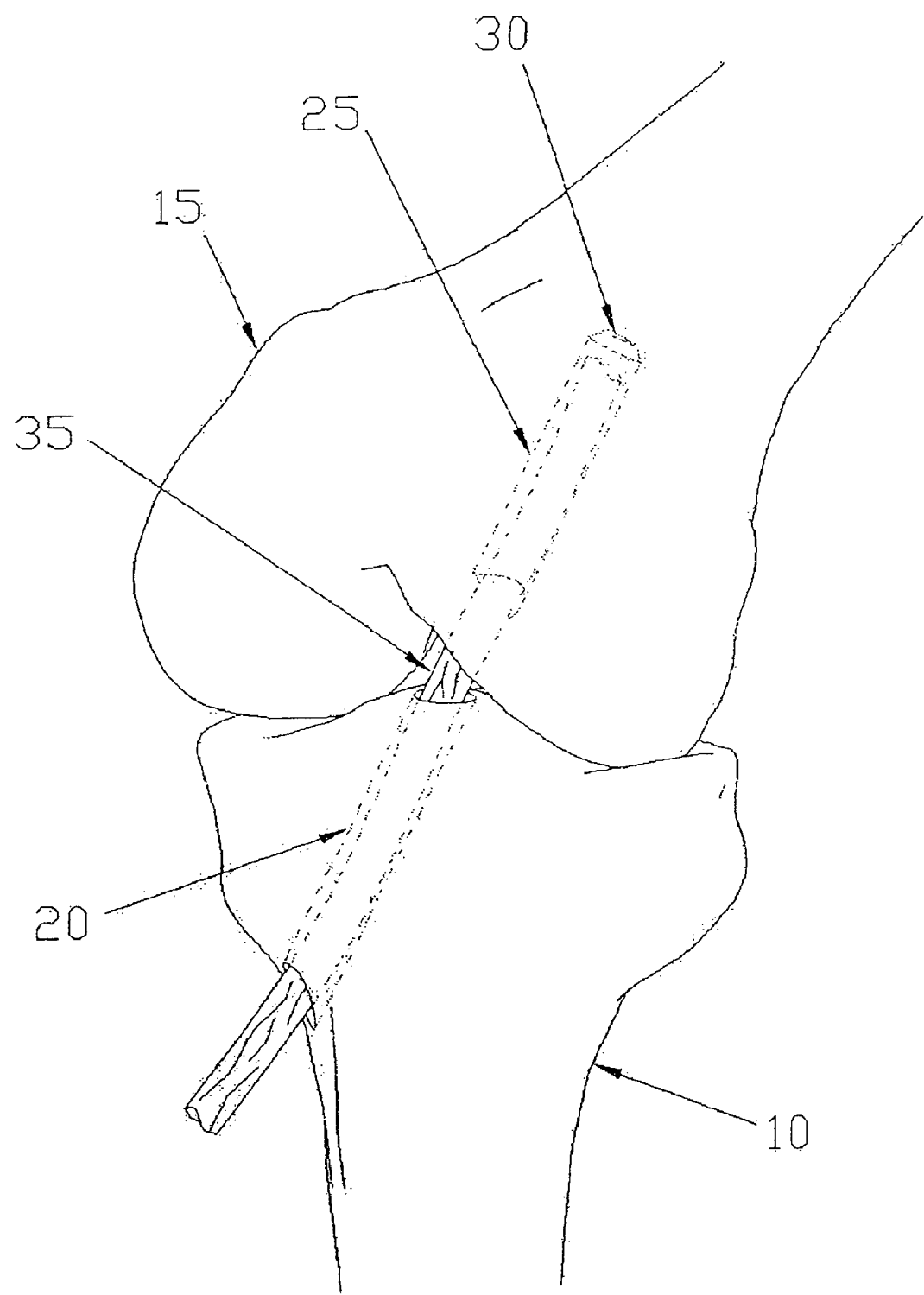
FIG. 3 is a schematic view of a generic ACL reconstruction.
Figure 4:
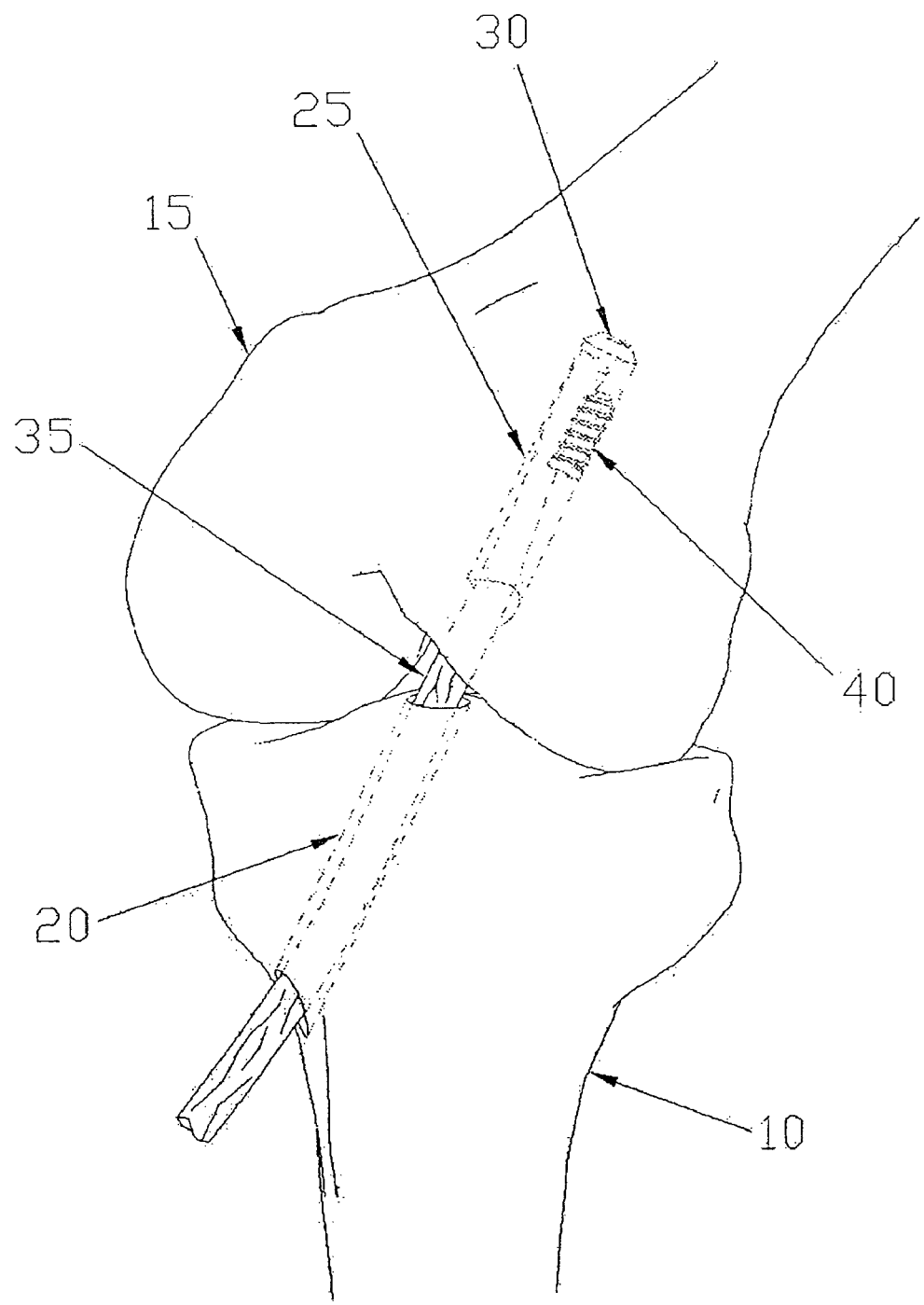
FIG. 4 is a schematic view of an ACL reconstruction effected using an interference screw.
Figure 5:
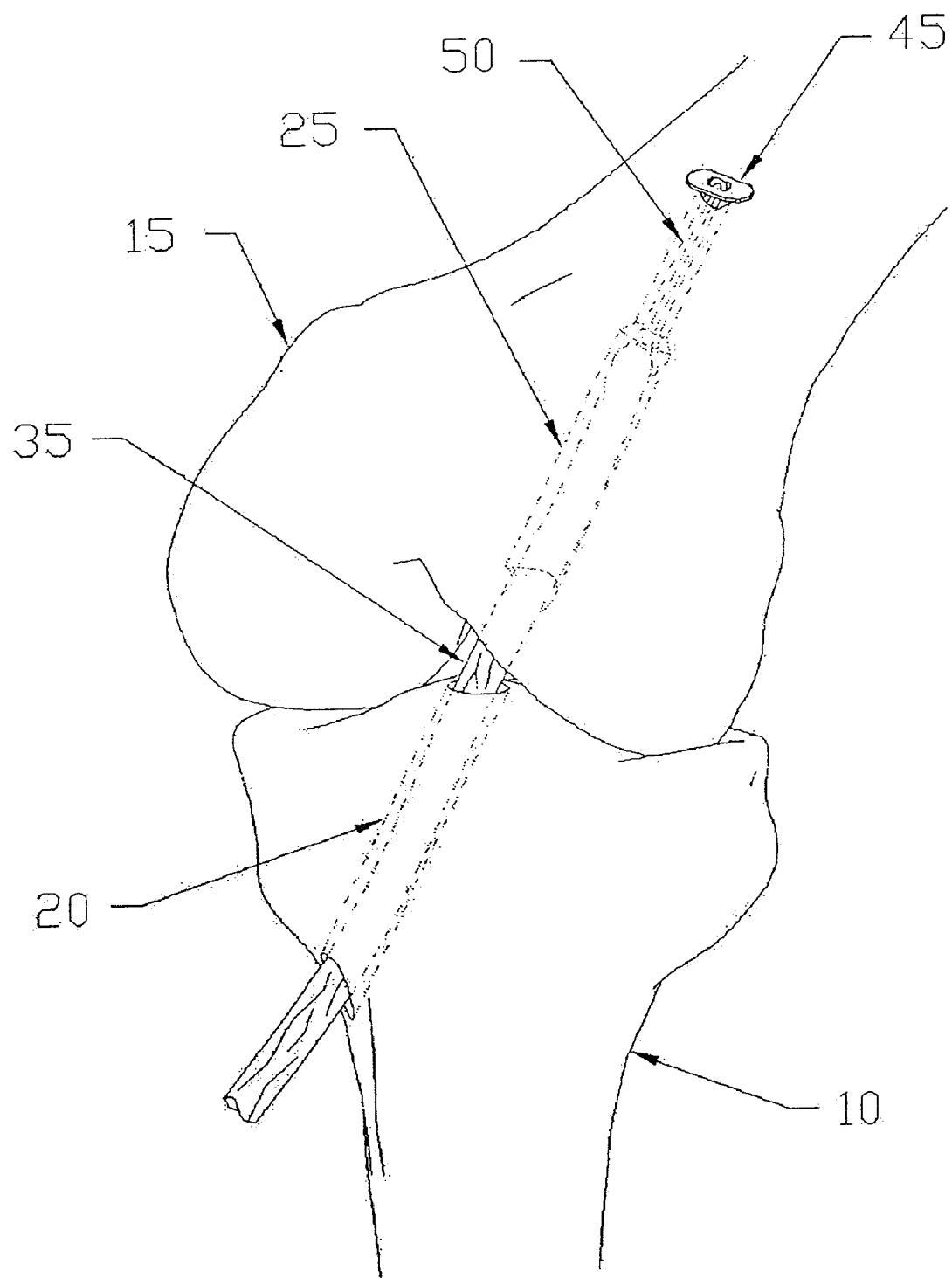
FIG. 5 is a schematic view of an ACL reconstruction effected using a suture sling.
Figure 6:
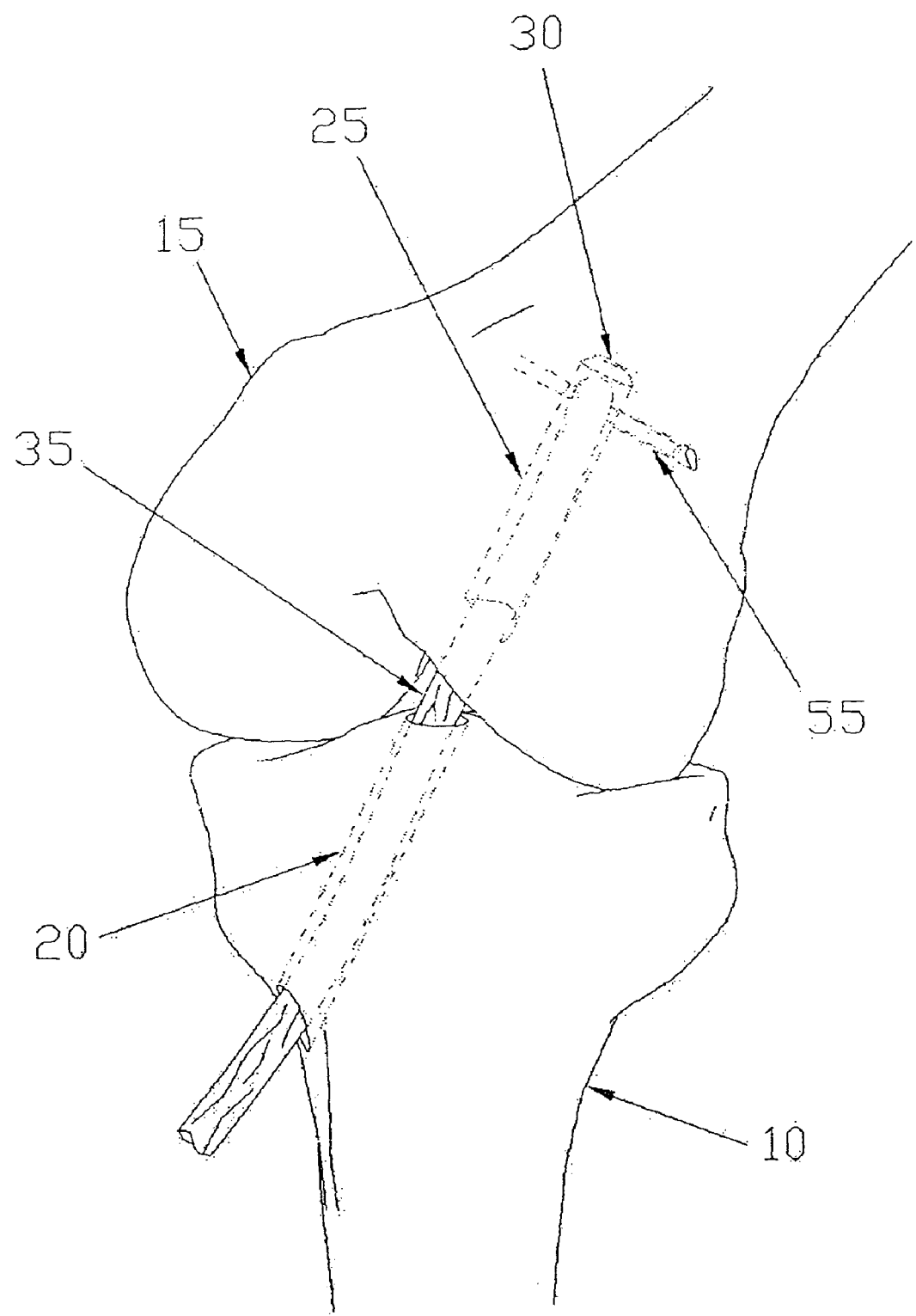
FIG. 6 is a schematic view of an ACL reconstruction effected using a crosspin.
Figure 7:
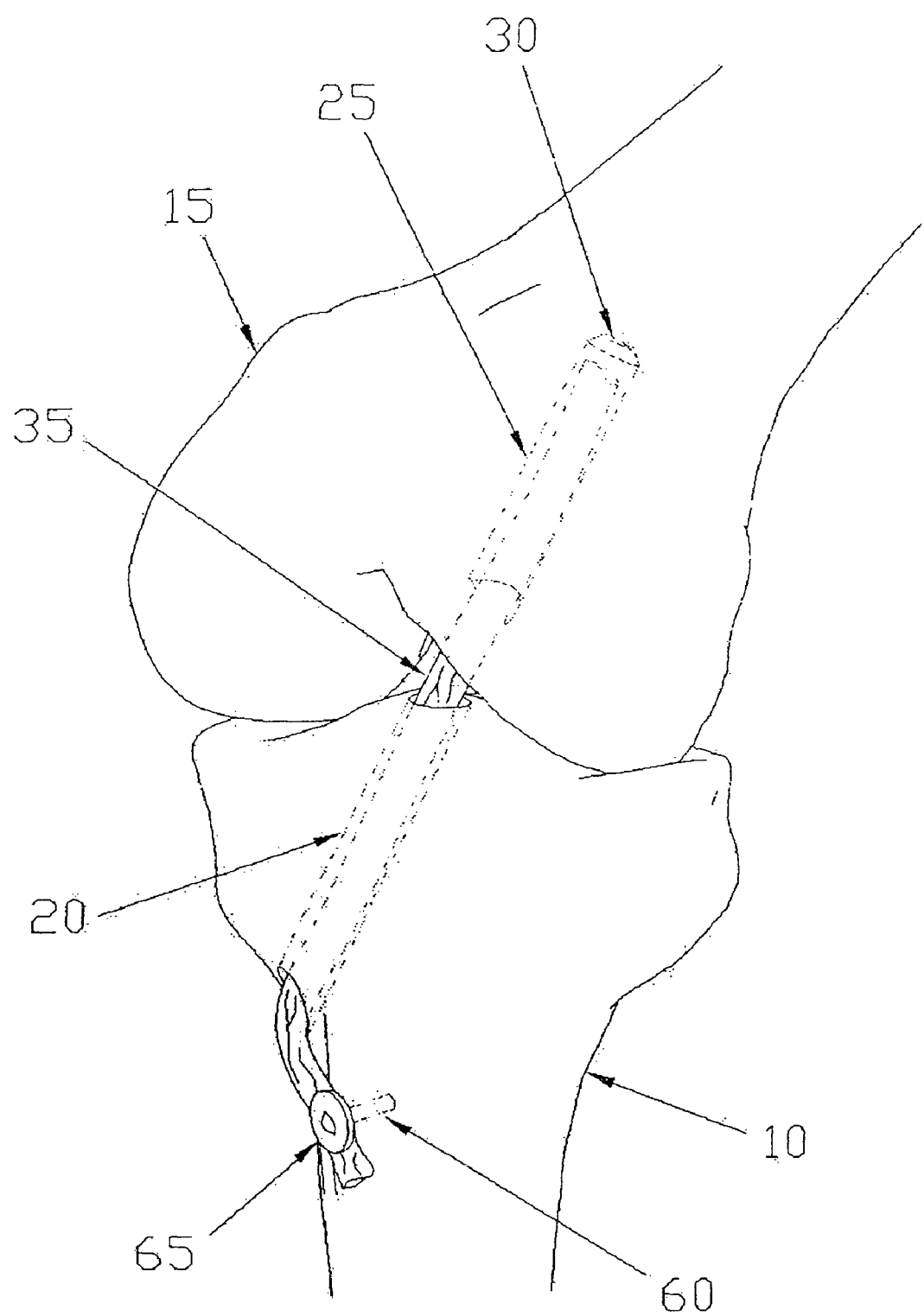
FIG. 7 is a schematic view of an ACL reconstruction effected using a screw and washer.
Figure 8:
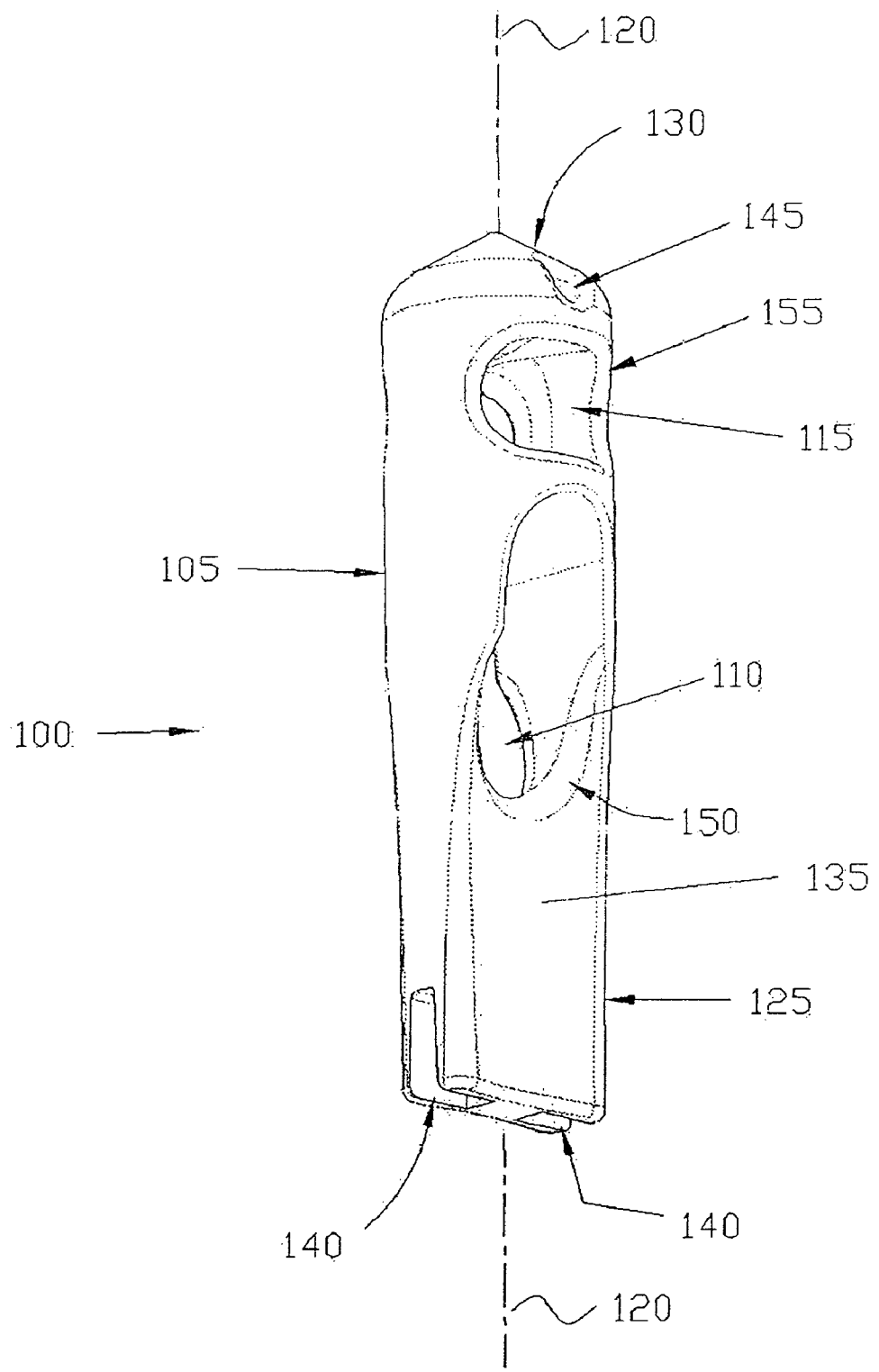
FIG. 8 is a schematic view of a graft ligament support block formed in accordance with the present invention.
Figure 9:
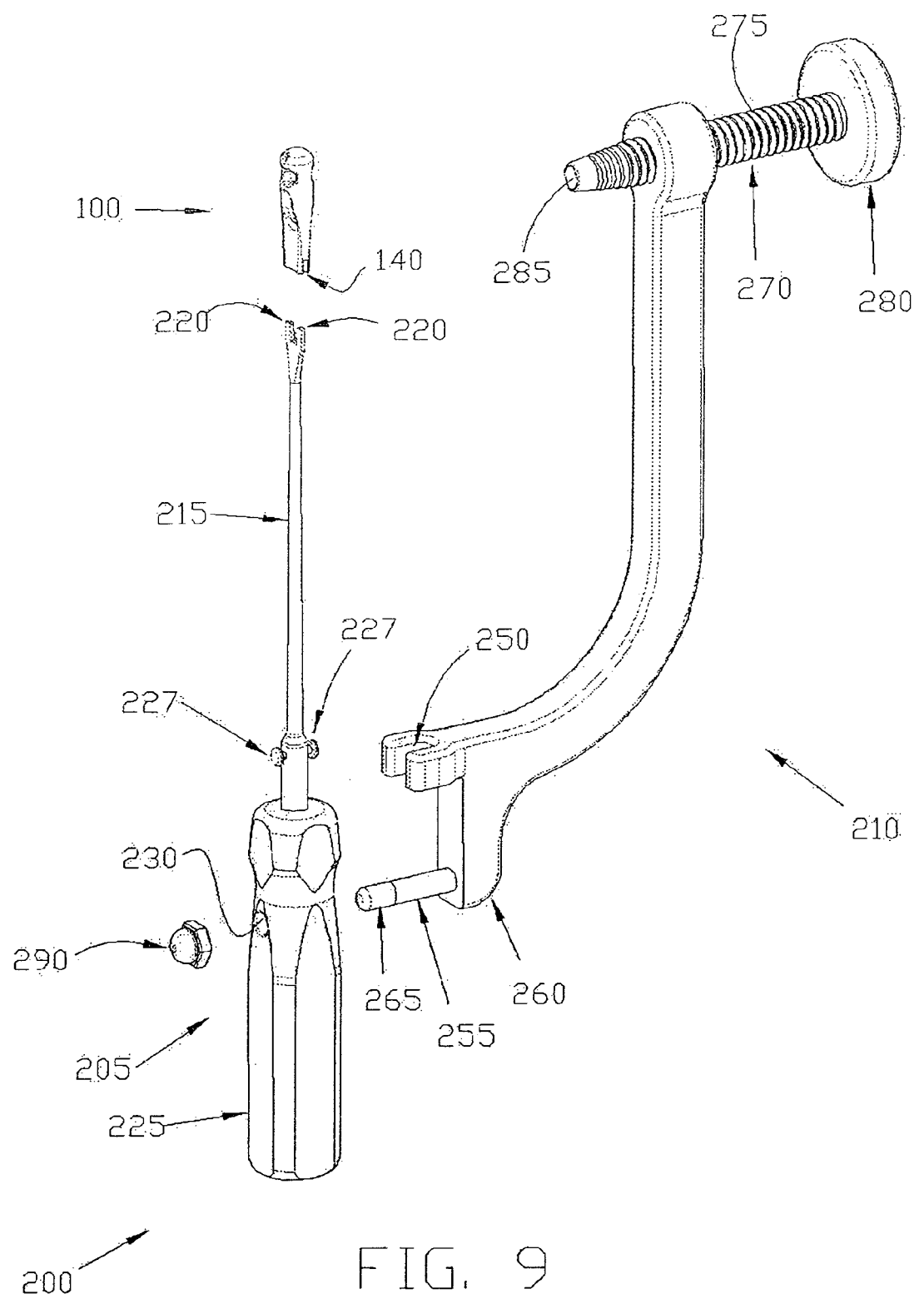
FIG. 9 is a partially exploded view showing the graft ligament support block of FIG. 8 and an installation tool for deploying the same.
Figure 10:
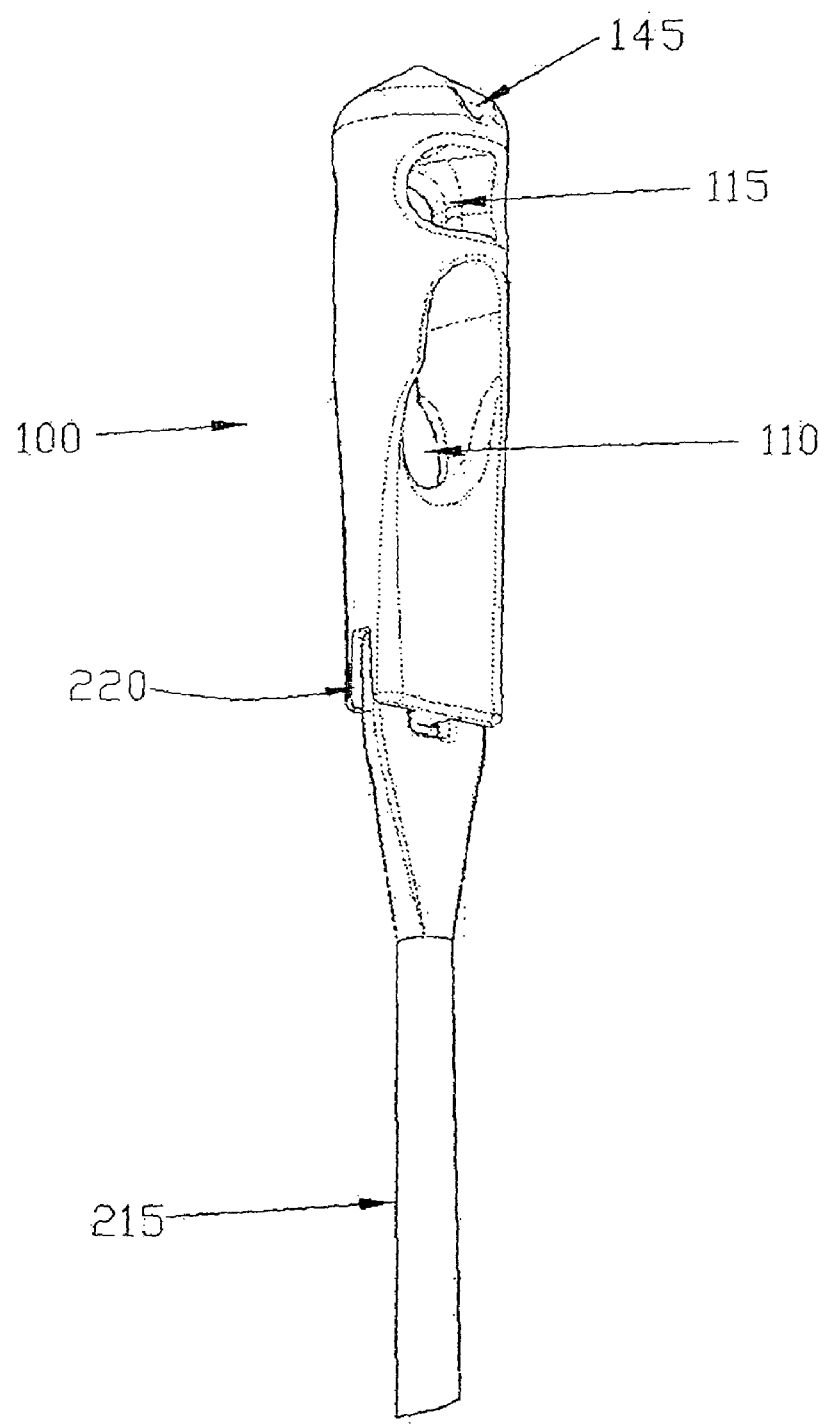
FIGS. 10-12 are various views showing the graft ligament support block of FIG. 8 mounted to the distal end of the installation tool shown in FIG. 9.
Figure 11:
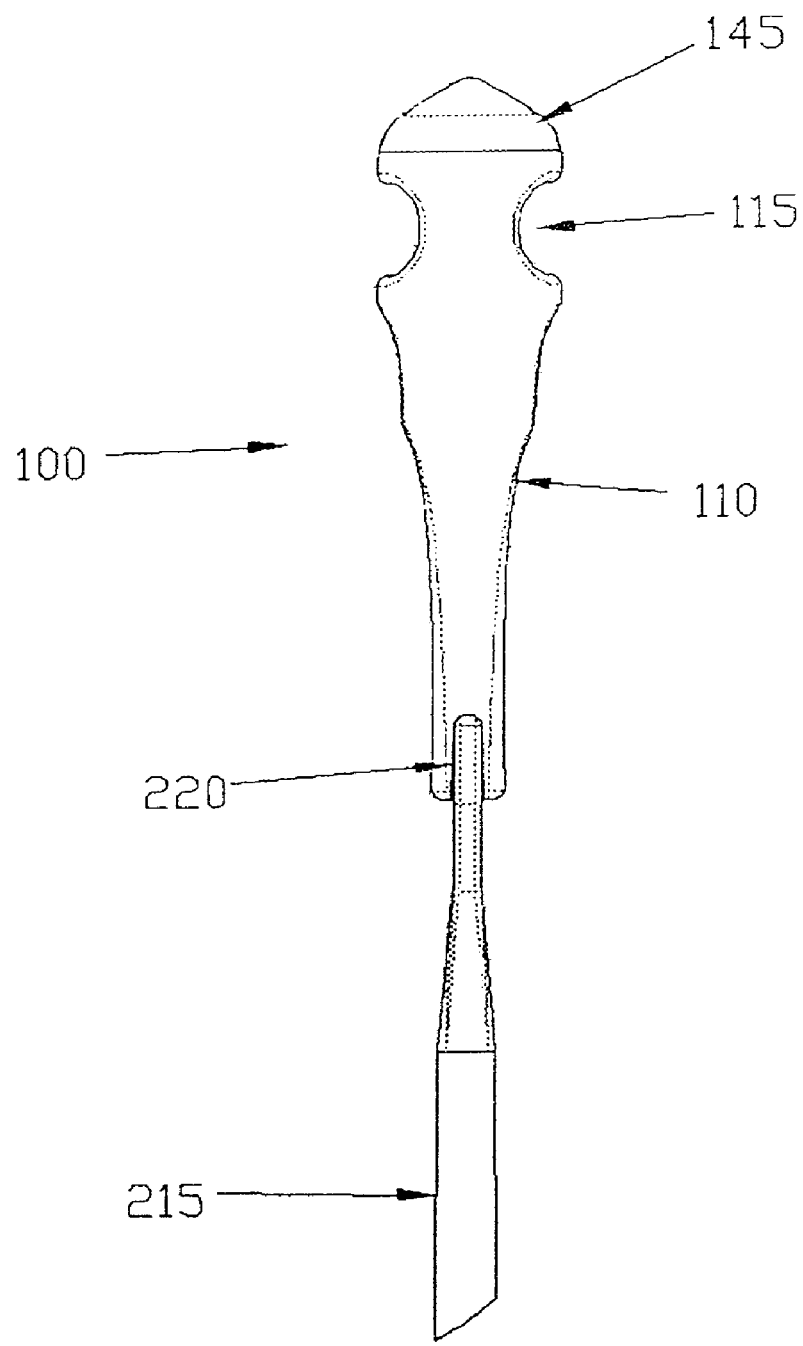
Figure 12:
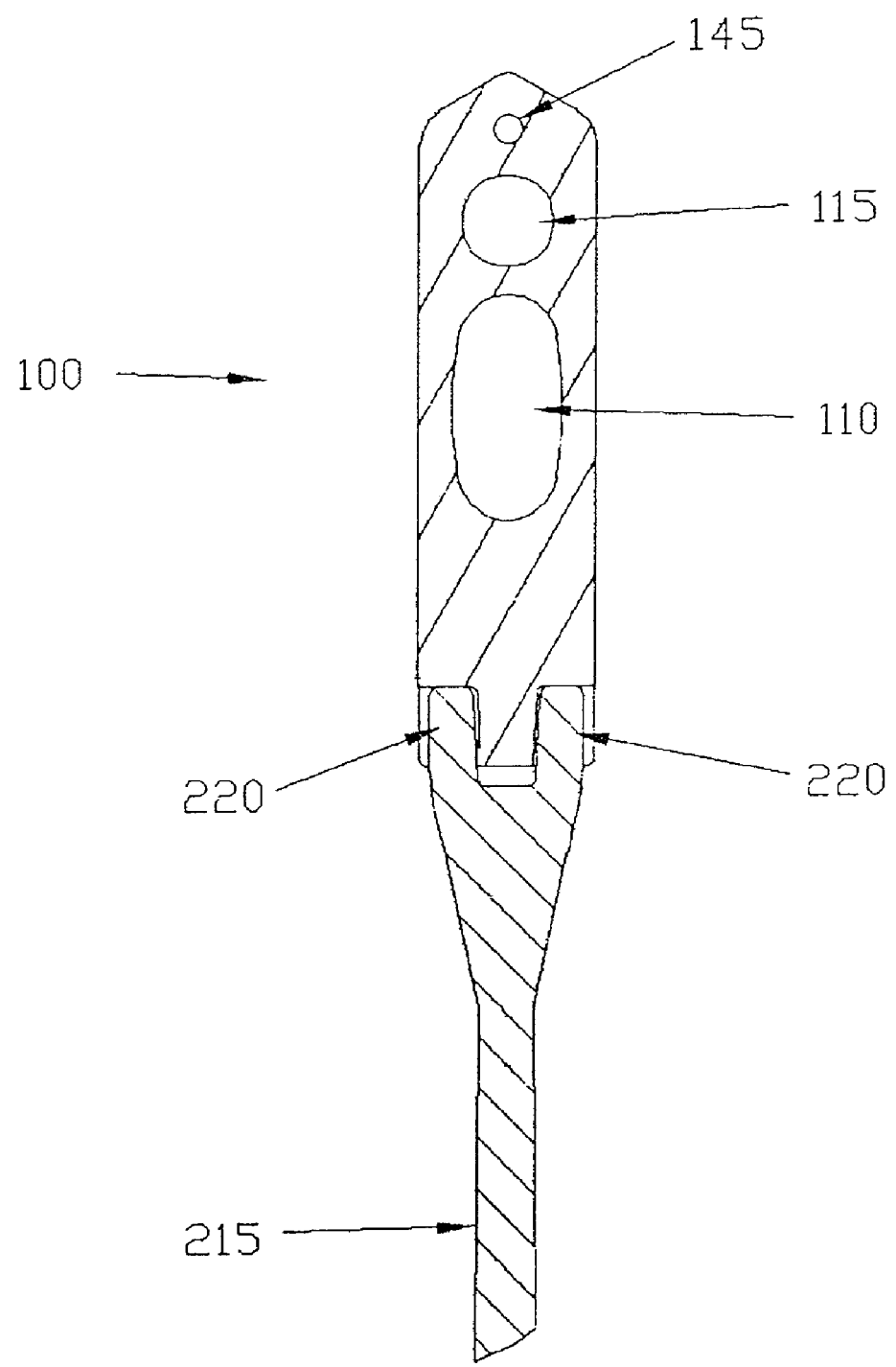
Figure 13:
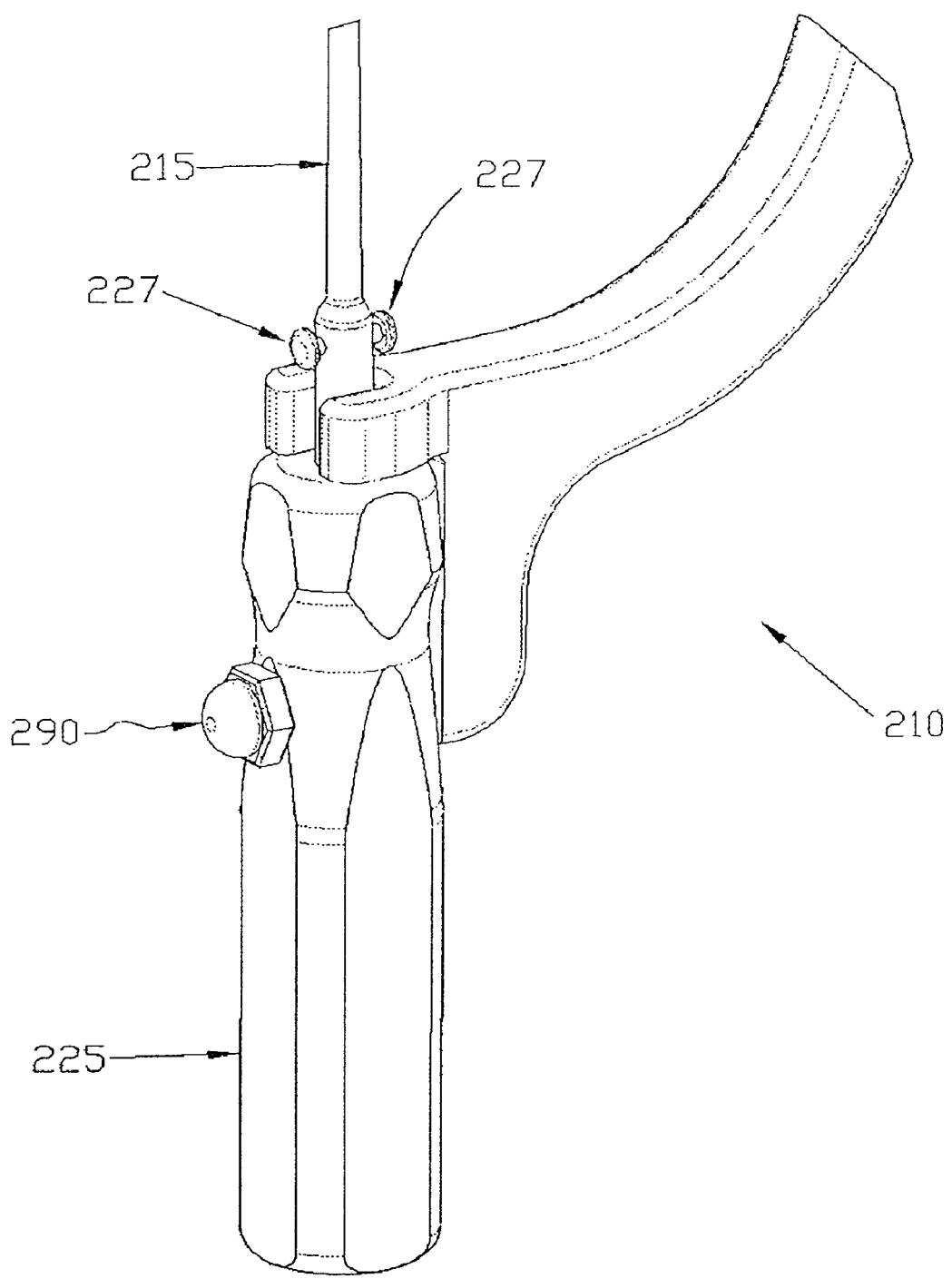
FIG. 13 is a partial perspective view showing details of the proximal end of the installation tool shown in FIG. 9.
Figure 14:
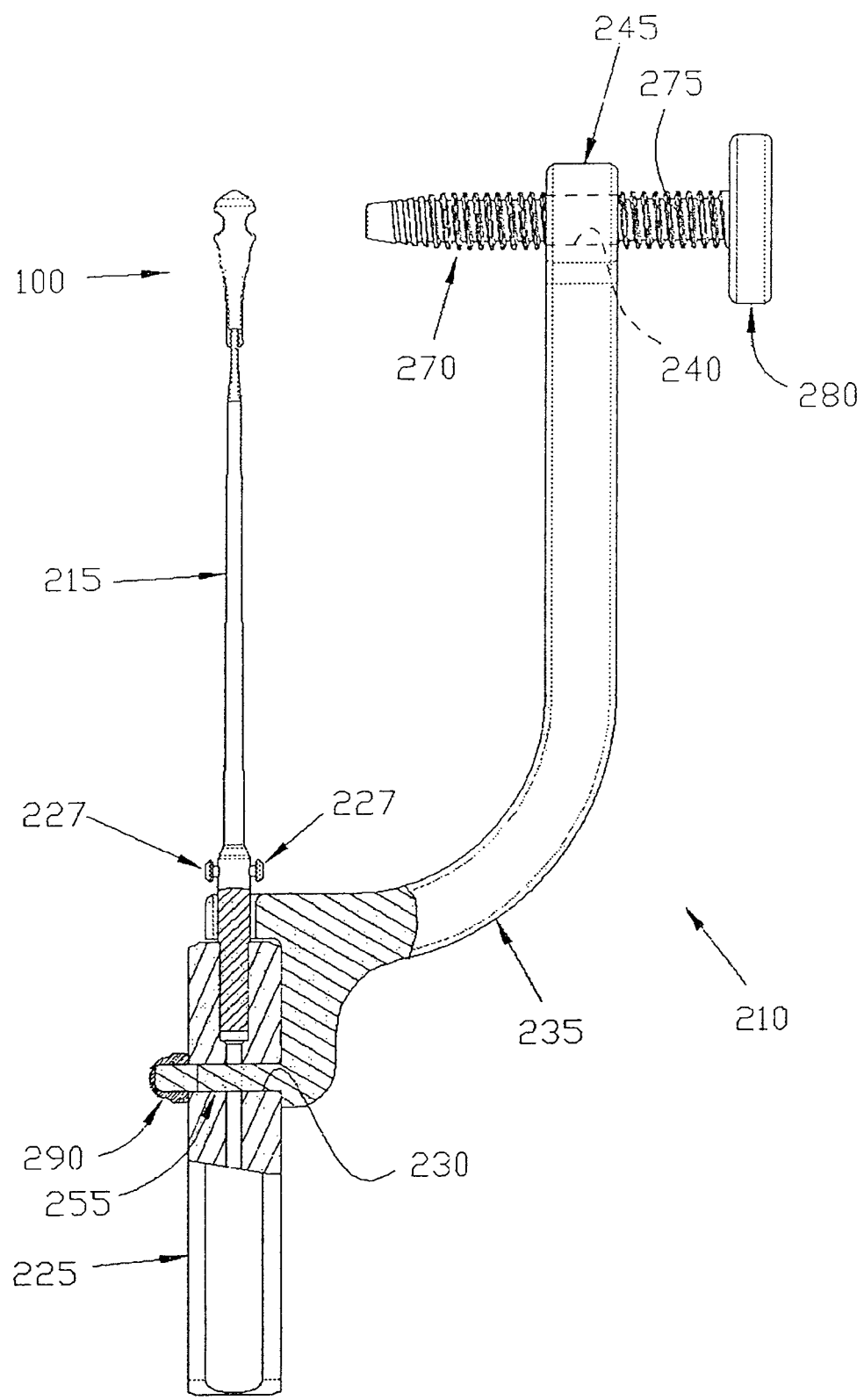
FIG. 14 is a side view, partially in section, showing further details of the construction of the installation tool shown in FIG. 9.
Figure 15:
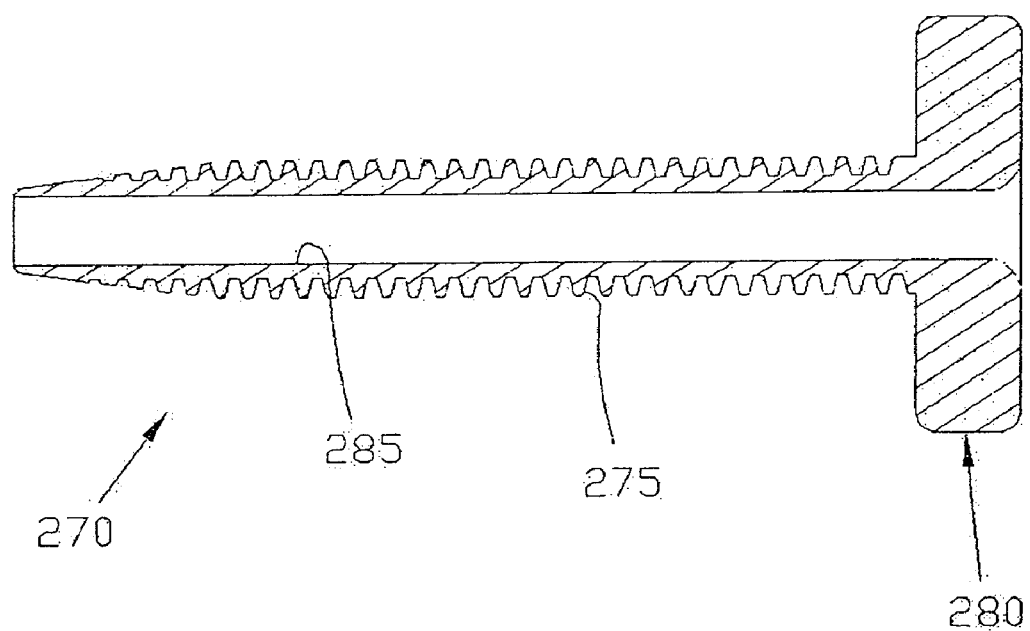
FIG. 15 is a side sectional view of the installation tool's drill sleeve.

Looking next at FIG. 8, there is shown a graft ligament support block 100 which comprises one preferred form of the invention. Graft ligament support block 100 comprises a body 105, and a graft hole 110 and a transverse fixation pin hole 115 extending through body 105, with both graft hole 110 and transverse fixation pin hole 115 preferably extending substantially perpendicular to the longitudinal axis 120 of body 105. In one preferred form of the invention, graft hole 110 and transverse fixation pin hole 115 extend diametrically across body 105, with graft hole 110 and transverse fixation pin hole 115 extending substantially parallel to one another. Preferably graft hole 110 resides closer to the proximal end 125 of body 105 than transverse fixation pin hole 115, and transverse fixation pin hole 115 resides closer to the distal end 130 of body 105 than graft hole 110. In one preferred form of the invention, the distal end of body 105 has a circular cross-section, although it may also have an oval cross-section or a polygonal cross-section (e.g., square or rectangular or triangular, etc.). In one preferred construction, the distal end of body 105 has a cross-section sized just slightly smaller than the diameter of the bone tunnel, so as to provide a close interface between body 105 and the walls of the bone tunnel. In one preferred form of the invention, the distal end 130 of body 105 is tapered so as to facilitate advancement of graft ligament support block 100 through a bone tunnel. And in a preferred form of the invention, the proximal end of body 105 is sculpted away, e.g. such as shown at 135, so as to provide more room for a graft ligament looped through graft hole 110 and extending distally therefrom. Body 105 also includes a pair of recesses 140 for mounting body 105 to an appropriate installation tool, as will hereinafter be discussed in further detail.

If desired, graft ligament support block 100 may also include suture hole 145 for receiving a tow suture, as will hereinafter be discussed in further detail.

Additionally, if desired, the proximal end of graft hole 110 may be tapered as shown at 150 so as to provide a less traumatic bearing surface for a graft ligament looped through graft hole 110, and/or the entrance of transverse fixation pin hole 115 may be tapered as shown at 155 so as to facilitate entry of a transverse fixation pin into transverse fixation pin hole 115.

Body 105 may be formed out of a polymer, a bioabsorbable or bioremodelable material, allograft bone, a metal, a ceramic, coral, a fiber composite, a composite including at least one of the foregoing, etc. By forming body 105 out of a relatively strong material, the graft ligament can be held under tension even where body 105 is relatively small, or where one or more of the holes 110, 115 and/or 145 is located fairly close to the periphery of body 105.

Looking next at FIGS. 9-15, there is shown an installation tool 200 which may be used in conjunction with graft ligament support block 100. Installation tool 200 generally comprises a holder 205 and an associated drill guide 210.

Holder 205 comprises a shaft 215 having a pair of finger 220 at its distal end and a handle 225 at its proximal end. Fingers 220 allow installation tool 200 to mate with, and releasably hold, graft ligament support block 100 by selectively fitting into the recesses 140 (FIG. 8) formed on the proximal end of graft ligament support block 100. See FIGS. 9-12 and 14. In essence, fingers 220 and recesses 140 comprise a male/female connection; if desired, the locations of the male and female members may be reversed (i.e., with the male portion on support block 100 and the female portion on holder 205); or an alternative type of connection (e.g., a grasper) may be used. Preferably one or more suture posts 227 are formed on the proximal end of shaft 215 adjacent to handle 225. Suture posts 227 allow the two free ends of a graft ligament to be secured to the installation tool, as will hereinafter be discussed in further detail. Handle 225 allows installation tool 200 to be conveniently grasped by a user. Handle 225 includes a post hole 230. Post hole 230 allows drill guide 210 to be releasably secured to holder 205, as will hereinafter be discussed in further detail.

Drill guide 210 comprises an outrigger 235 having a threaded bore 240 (FIG. 14) formed in its distal end 245, and a slot 250 (FIG. 9) and post 255 at its proximal end 260. The end of post 255 is threaded, e.g., as shown at 265.

The threaded bore 240 (FIG. 14) in the outrigger's distal end 245 is sized to receive a drill sleeve 270 therein. Drill sleeve 270 has threads 275 along its length and terminates in a proximal head 280. Head 280 can be used to manually rotate drill sleeve 270 within the outrigger's threaded bore 240, whereby to move drill sleeve 270 relative to the distal end 245 of outrigger 235. A lumen 285 extends through drill sleeve 270.

Slot 250 and post 255 permit outrigger 235 to be releasably mounted to holder 205. More particularly, outrigger 235 may be mounted to holder 205 by fitting the holder's shaft 215 in the outrigger's slot 250 (FIGS. 13 and 14), fitting the outrigger's post 255 in the holder's post hole 230, and then tightening nut 290 onto the threaded end 265 of post 255.

Figure 16:
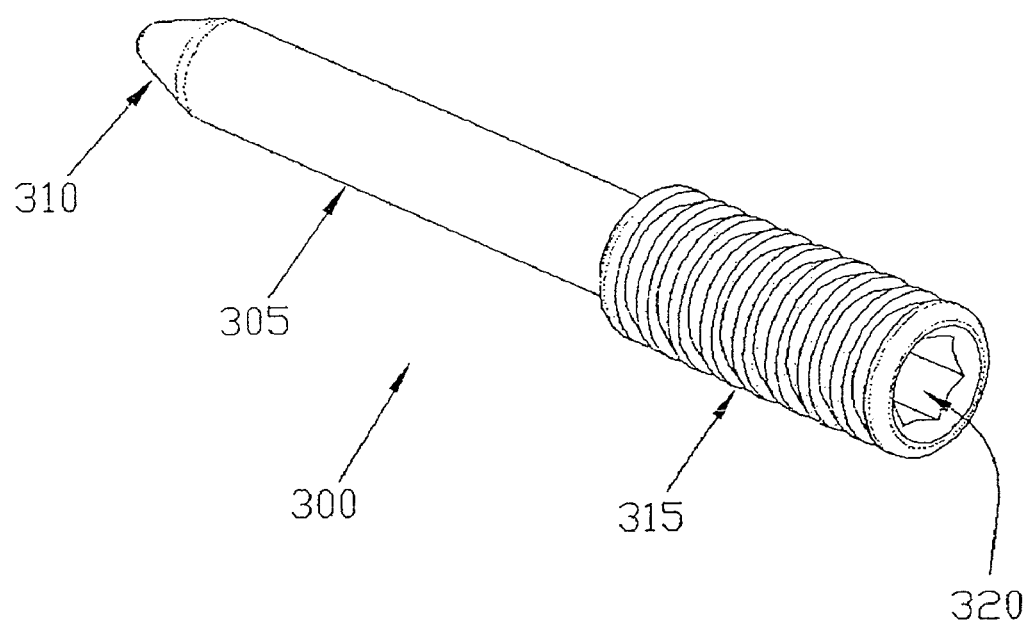
FIG. 16 is a perspective view of a transverse fixation pin which may be used in conjunction with the graft ligament support block of FIG. 8 and the installation tool of FIG. 9.

As will hereinafter be described, graft ligament support block 100 and installation tool 200 are intended to be used in conjunction with a transverse fixation pin. One preferred transverse fixation pin 300 is shown in FIG. 16. Transverse fixation pin 300 generally comprises a solid shaft 305 terminating in a tapered distal end 310, and a ribbed (or barbed or threaded) section 315. A non-circular socket 320 is formed in the proximal end of transverse fixation pin 300, whereby transverse fixation pin 300 may be engaged by a driver.

An ACL reconstruction effected in accordance with the present invention will now be described.

Figure 17:
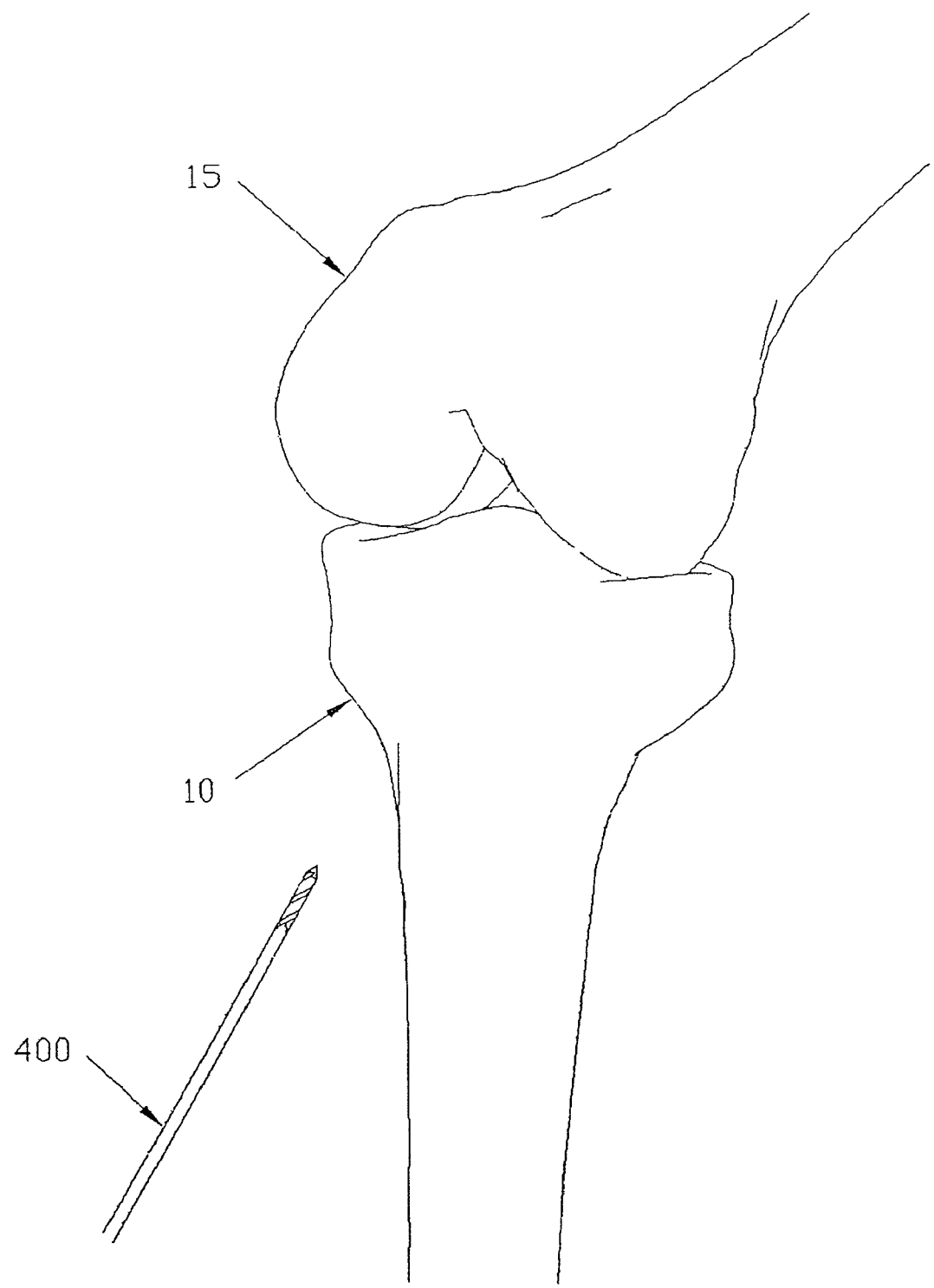
FIGS. 17-33 are a series of schematic views showing an ACL reconstruction being effected in accordance with the present invention.
Figure 18:
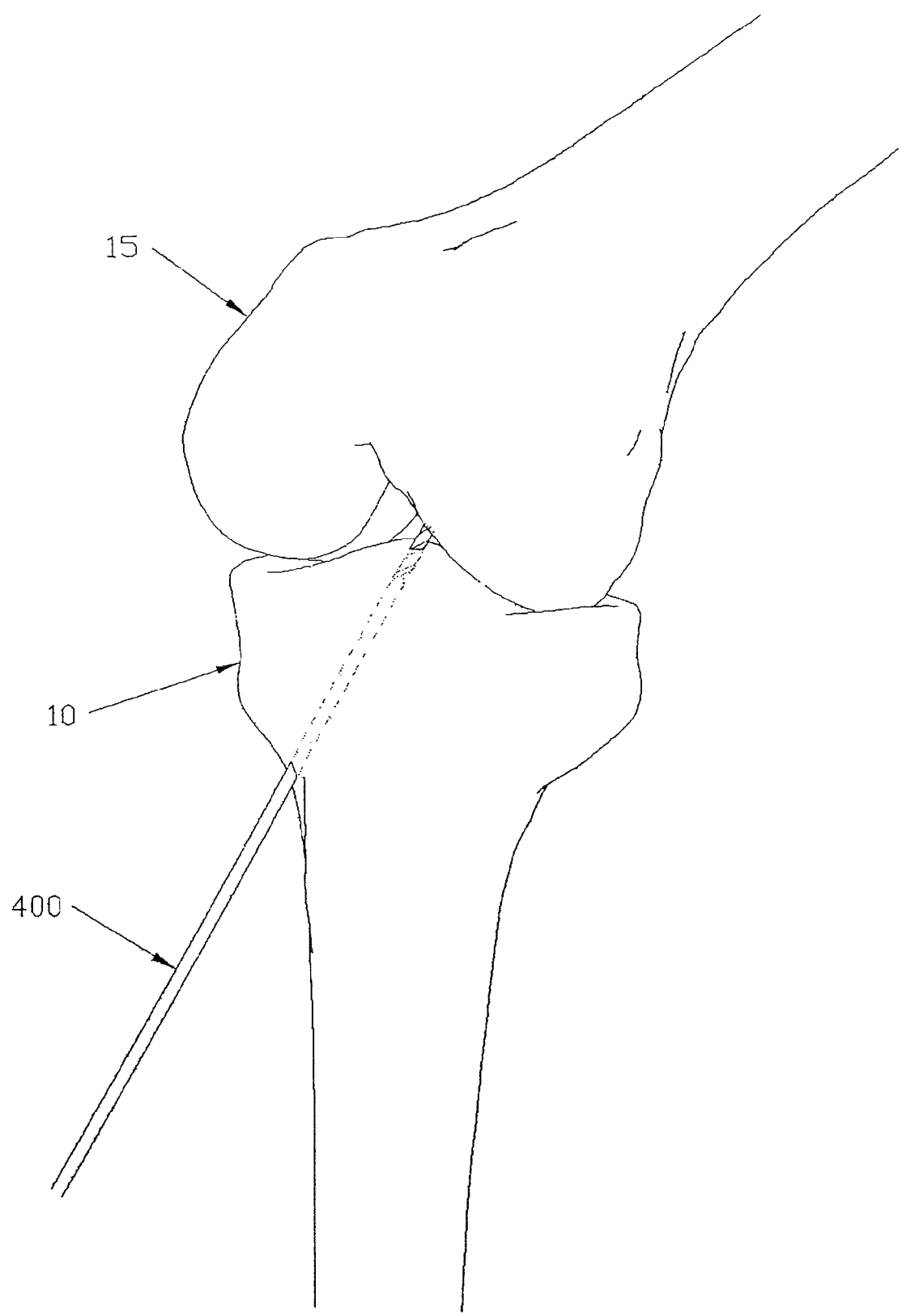
Figure 19:
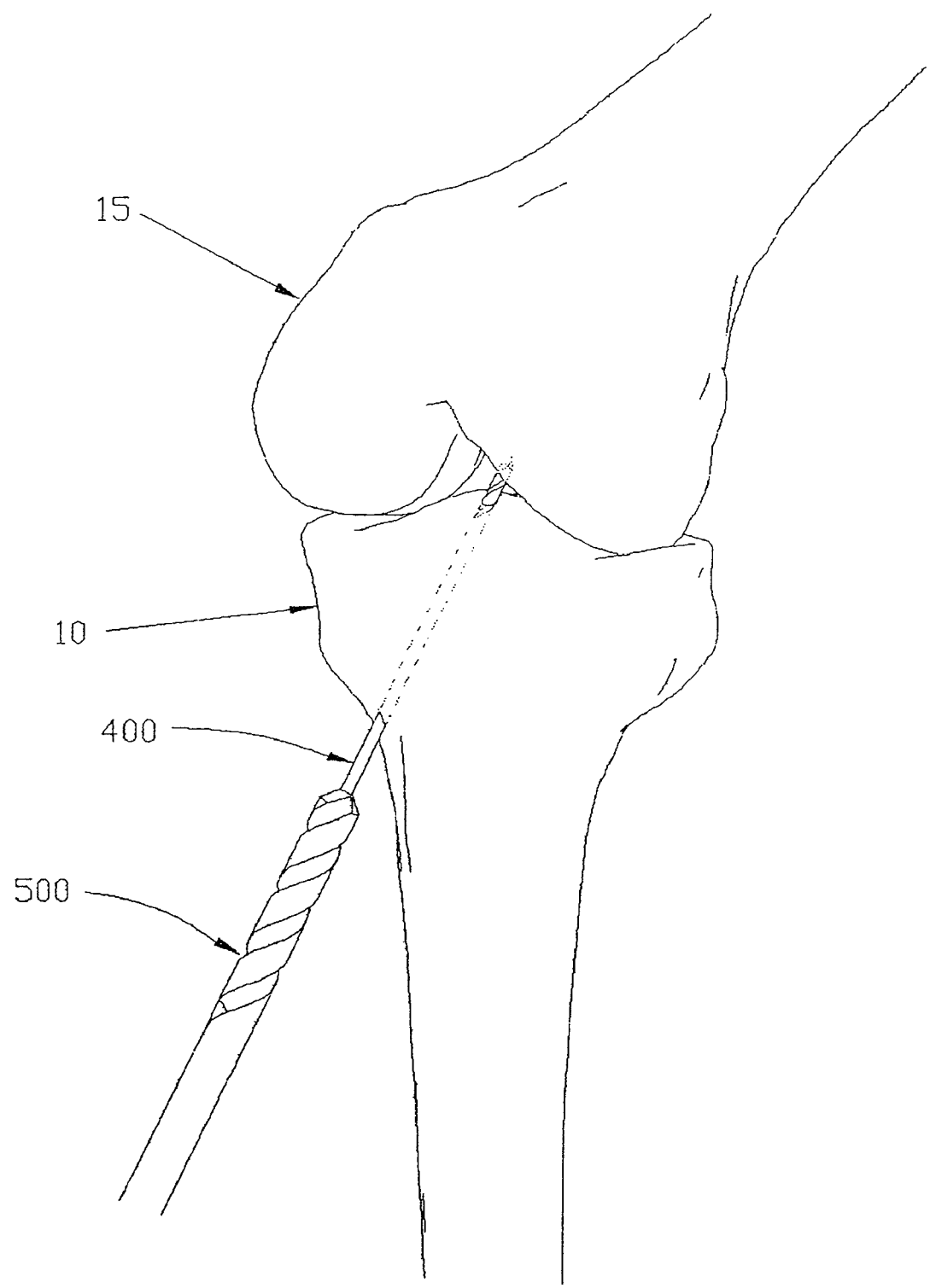
Figure 20:
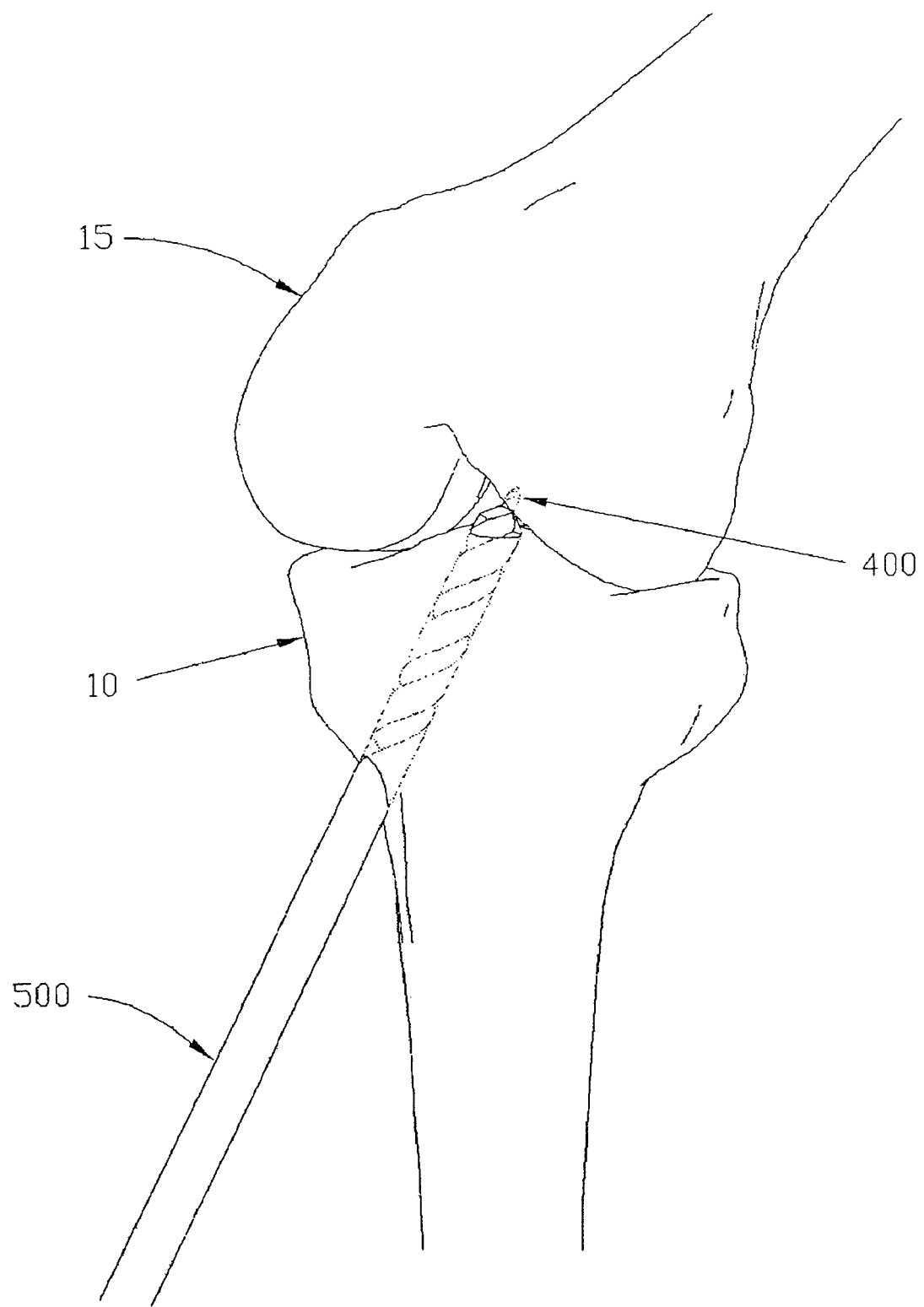
Figure 21:
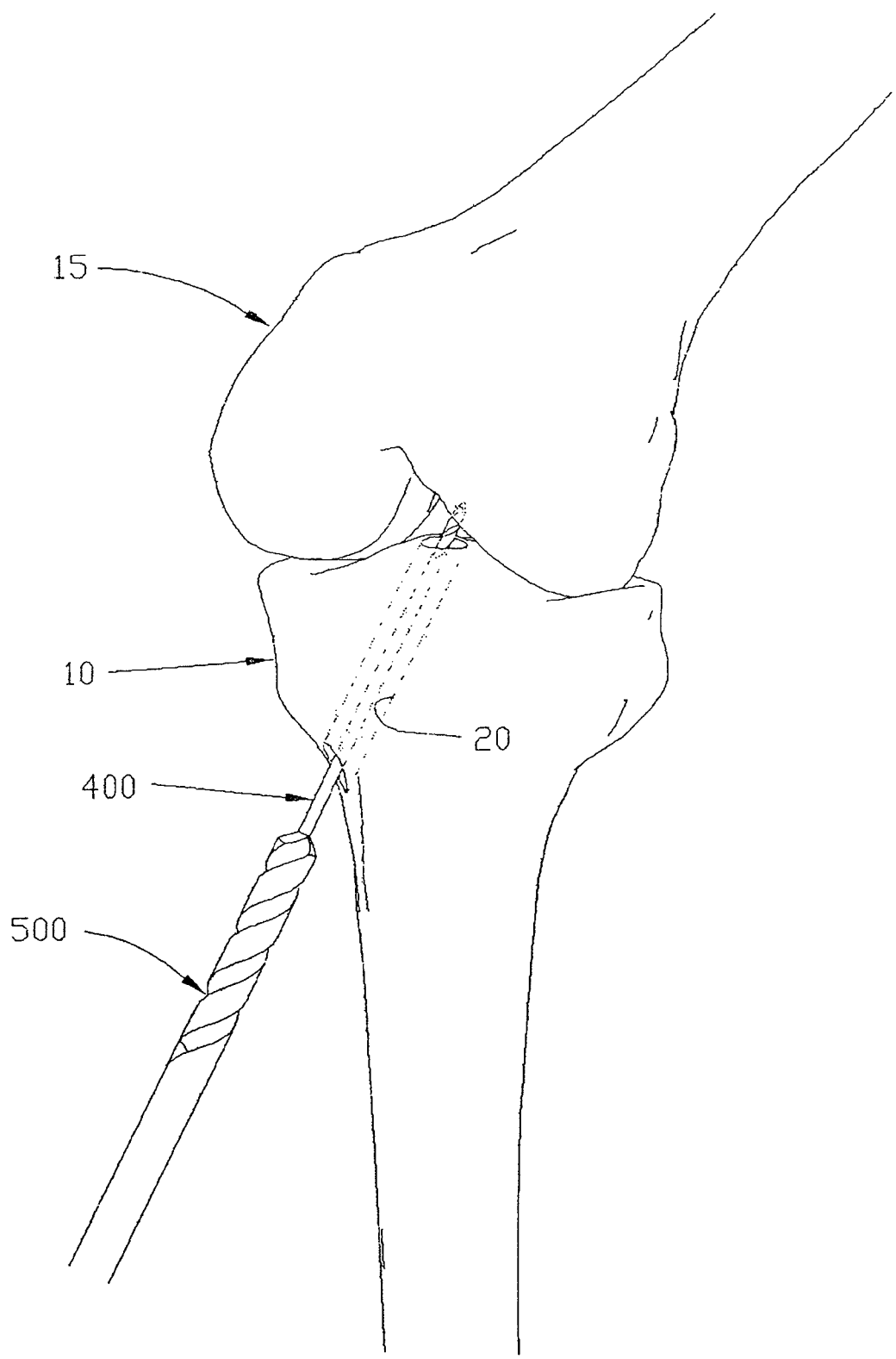

First, the surgical site is prepared for the graft ligament, e.g., by clearing away the damaged ACL, etc. Then a guidewire 400 (FIG. 17) is drilled up through tibia 10 and into the interior of the knee joint. Preferably guidewire 400 is stopped short of engaging the bottom of femur 15 (FIG. 18). Then a cannulated tibial drill 500 (FIG. 19) is loaded onto guidewire 400 and drilled up through tibia 10 and into the interior of the knee joint (FIG. 20). Then cannulated tibial drill 500 is withdrawn back down the guidewire (FIG. 21), leaving a tibial tunnel 20.

Figure 22:
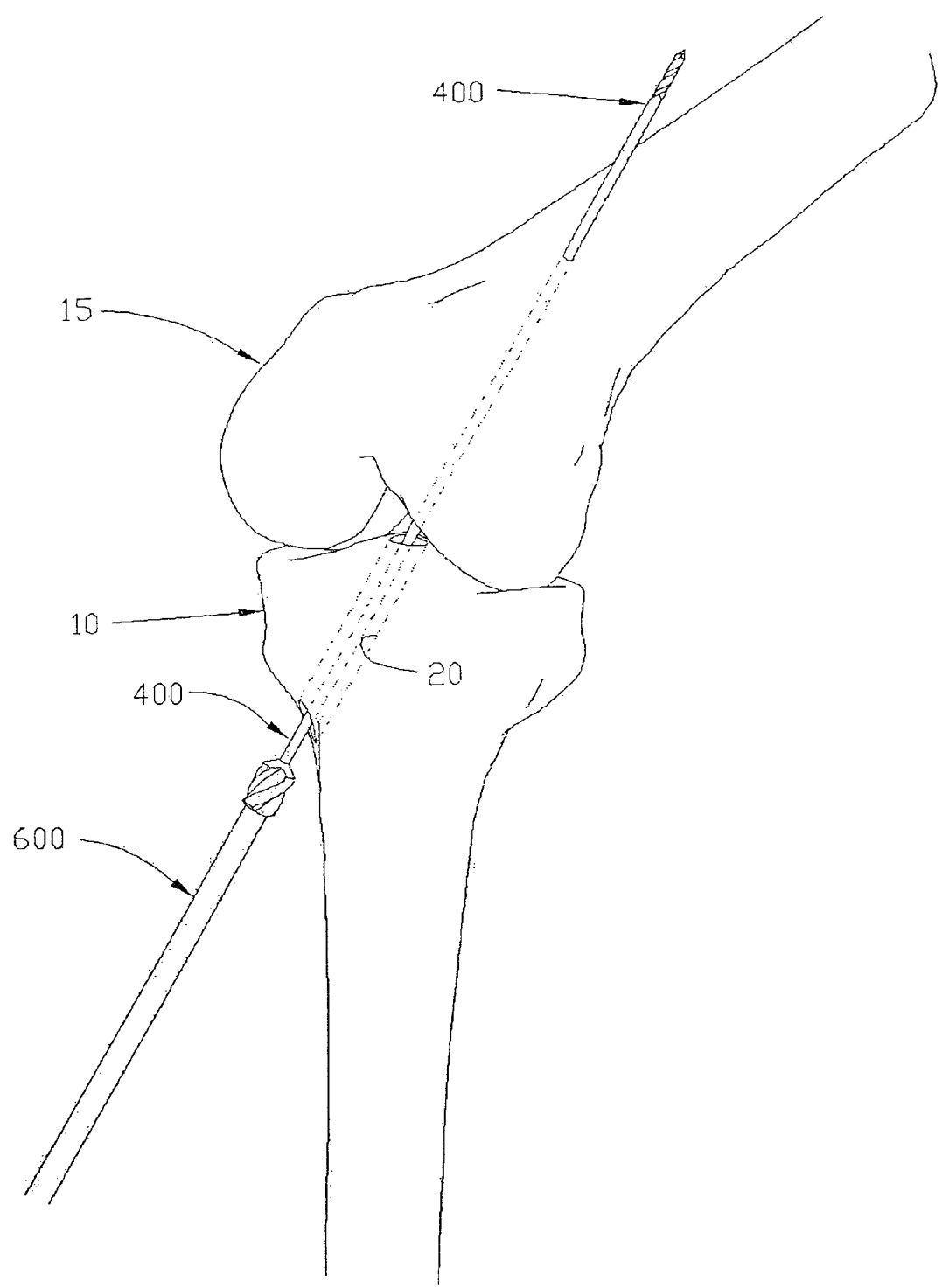
Figure 23:
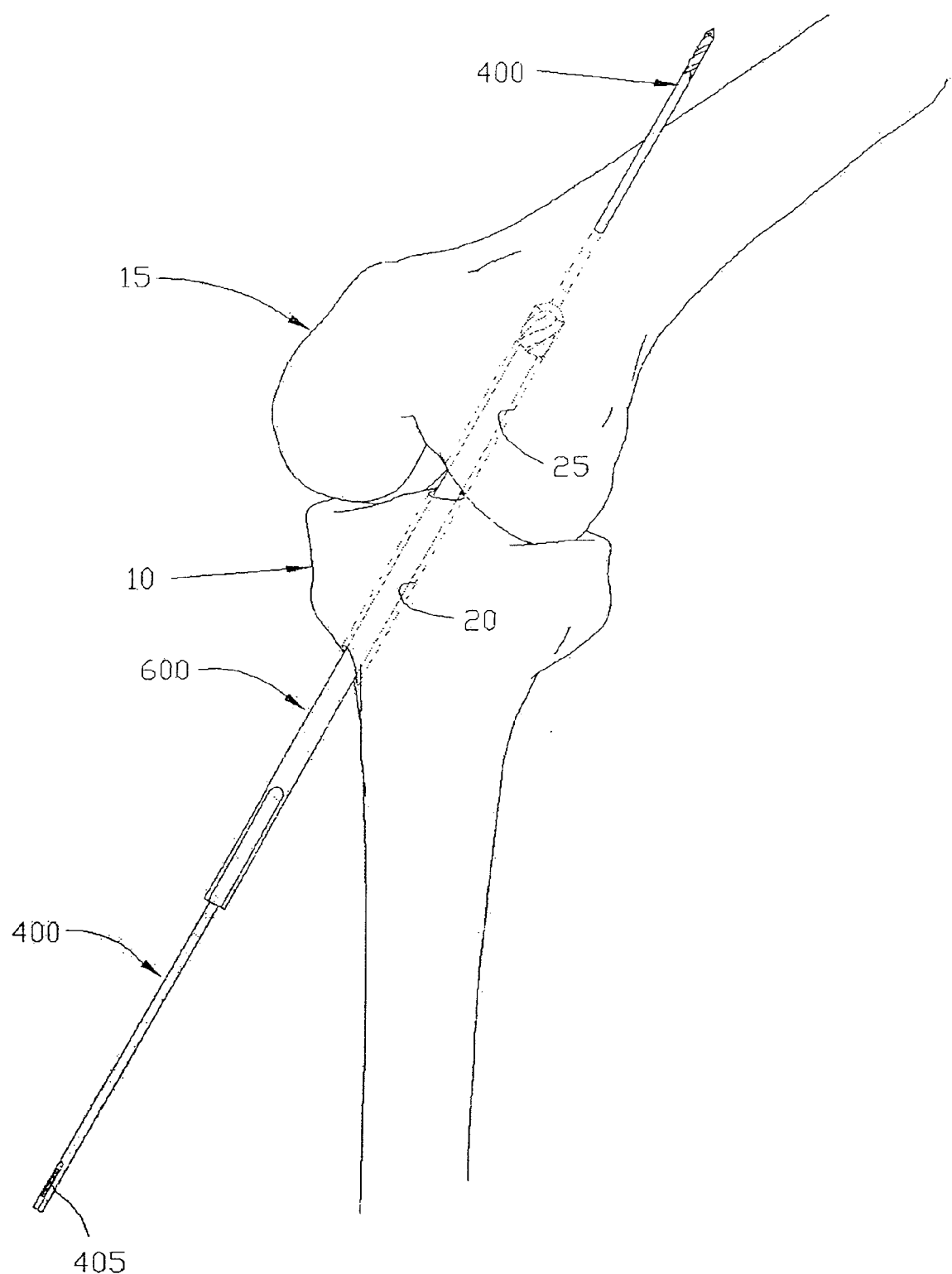
Figure 24:
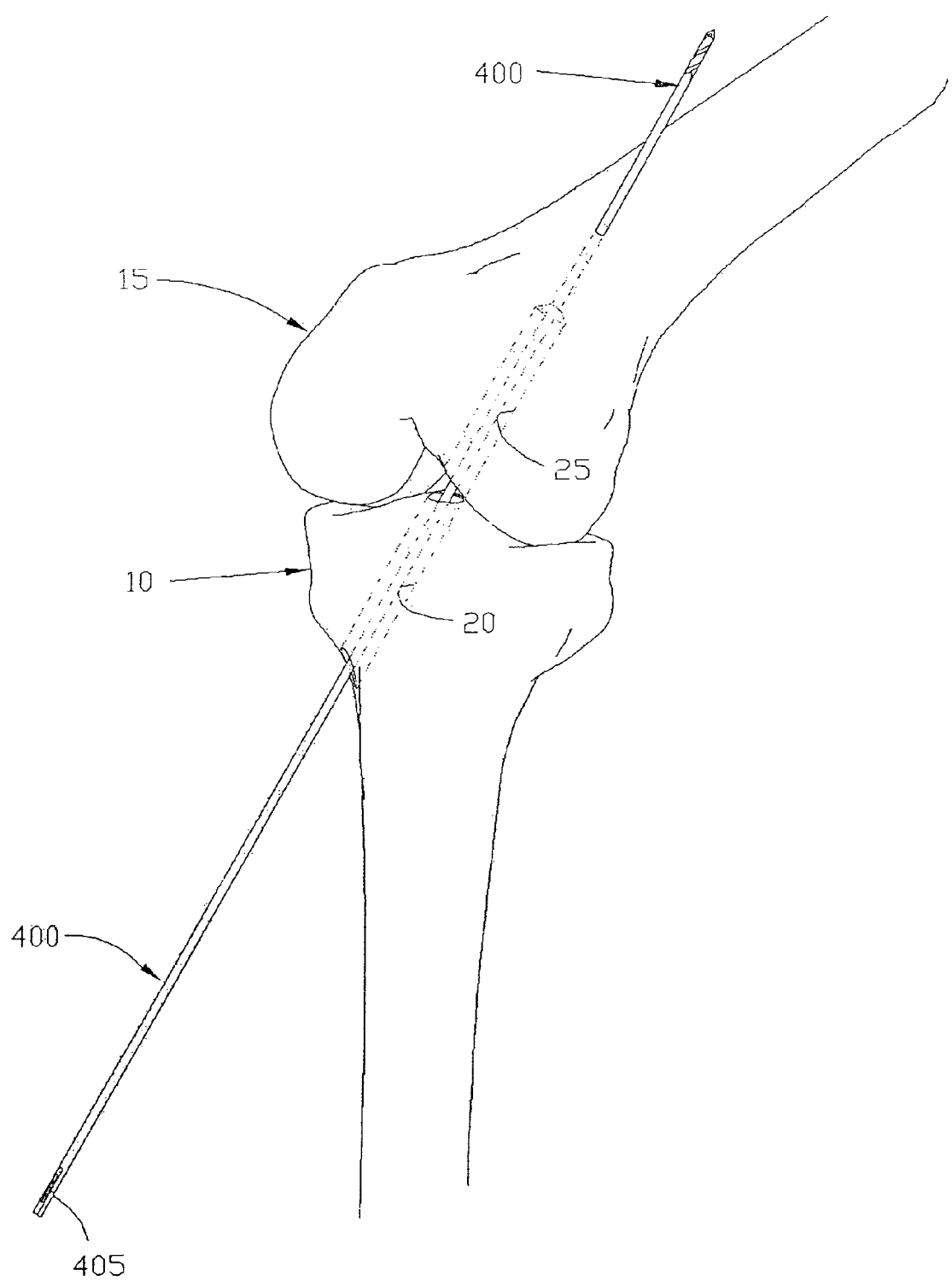

Next, guidewire 400 is drilled an appropriate distance into the interior of femur 15. If desired, guidewire 400 may be drilled all the way through femur 15 (FIG. 22), for reasons which will hereinafter be described. Then a cannulated femoral drill 600 (e.g., an acorn drill) is loaded onto guidewire 400 (FIG. 22), passed through tibial tunnel 20, across the interior of the knee joint, and then drilled up into femur 15, stopping within the interior of femur 15 (FIG. 23). Then cannulated femoral drill 600 is withdrawn back down the guidewire, leaving a femoral tunnel 25 (FIG. 24).

Figure 25:
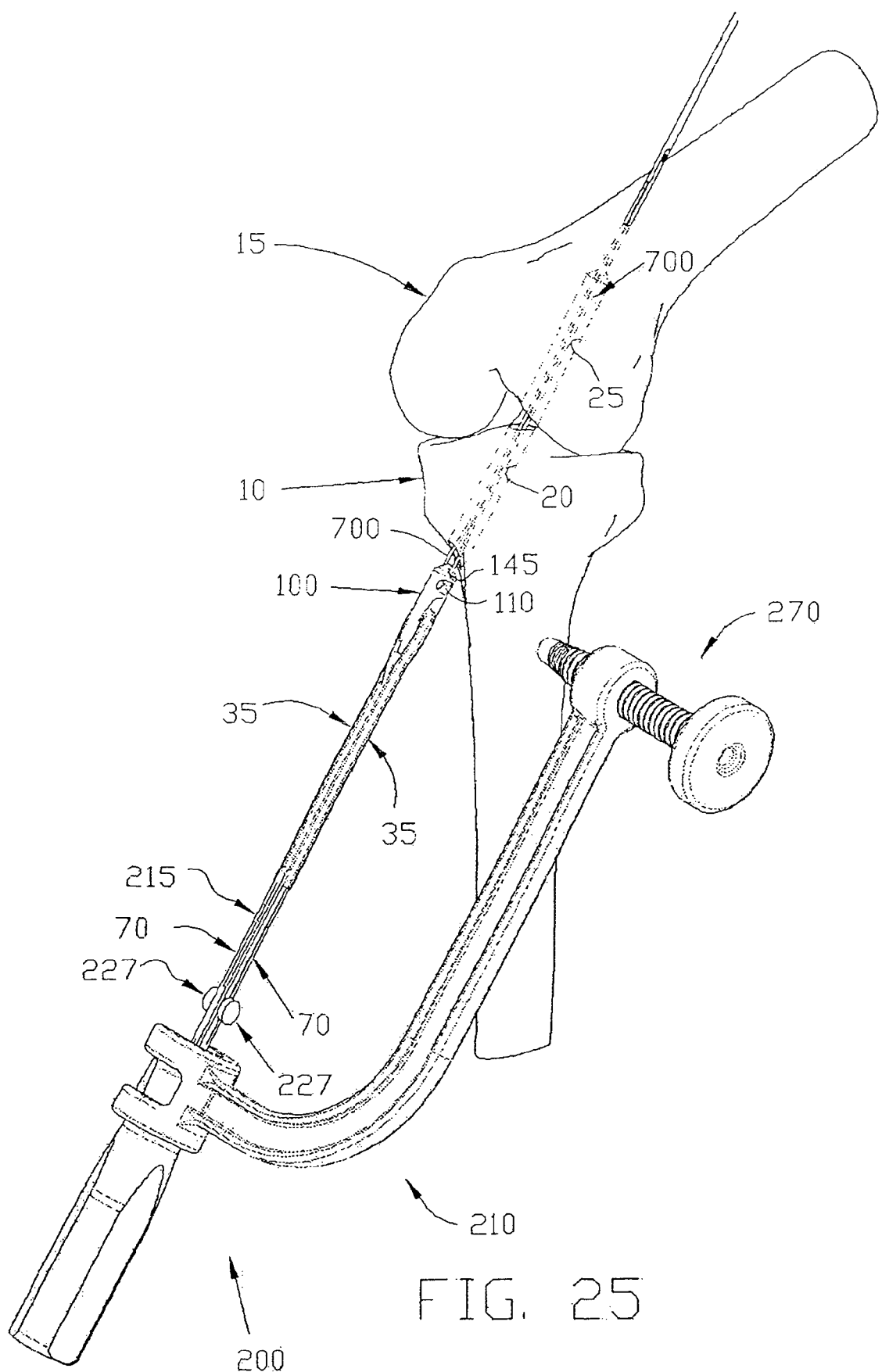
Figure 26:
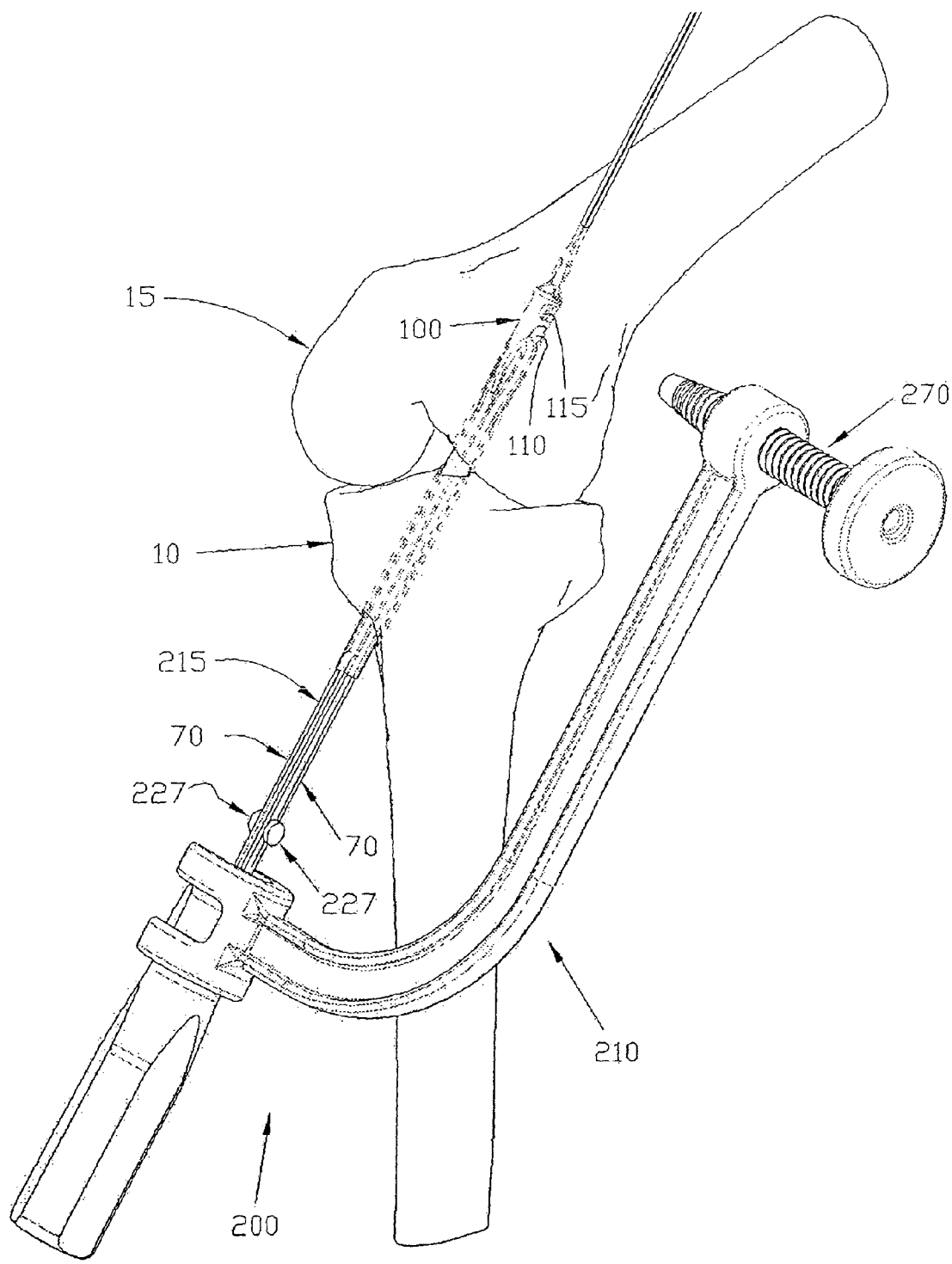

Next, a graft ligament 35 is mounted to graft ligament support block 100 by threading one end of the graft ligament through graft hole 110, and then graft ligament support block 100 is mounted to the distal end of shaft 215, i.e., by seating fingers 220 in recesses 140. The two free ends of graft ligament 35 are preferably held taut, e.g., by passing sutures 70 through the two free ends of graft ligament 35 and then securing those sutures (e.g., by winding) to suture posts 227. This arrangement will help control the two free ends of graft ligament 35 and will help hold graft ligament support block 100 to holder 205. Then installation tool 200 is used to push graft ligament support block 100, and hence graft ligament 35, up through tibial tunnel 20 (FIG. 25), across the interior of the knee joint, and up into femoral tunnel 25 (FIG. 26).

If desired, all of the force required to advance graft ligament support block 100 and graft ligament 35 through tibial tunnel 20, across the interior of the knee joint, and up into femoral tunnel 25 may be supplied by pushing distally on installation tool 200. Alternatively, if guidewire 400 has been drilled completely through femur 15 (e.g., such as is shown in FIG. 22), and if the proximal end of guidewire 400 includes a suture eyelet (e.g., such as the suture eyelet 405 shown in FIGS. 23 and 24), a suture may be used to help tow graft ligament support block 100 and graft ligament 35 up into position. More particularly, a suture 700 (FIG. 25) may be looped through the suture hole 145 in graft ligament support block 100 and through suture eyelet 405 on guidewire 400; then, by pulling distally on the portion of guidewire 400 extending out of the top end of femur 15, suture 700 can be used to help tow graft ligament support block 100 and graft ligament 35 up into position (FIG. 26). Such an arrangement will help reduce the amount of force which needs to be delivered by installation tool 200 to push graft ligament support block 100 and graft ligament 35 up into position.

Figure 27:
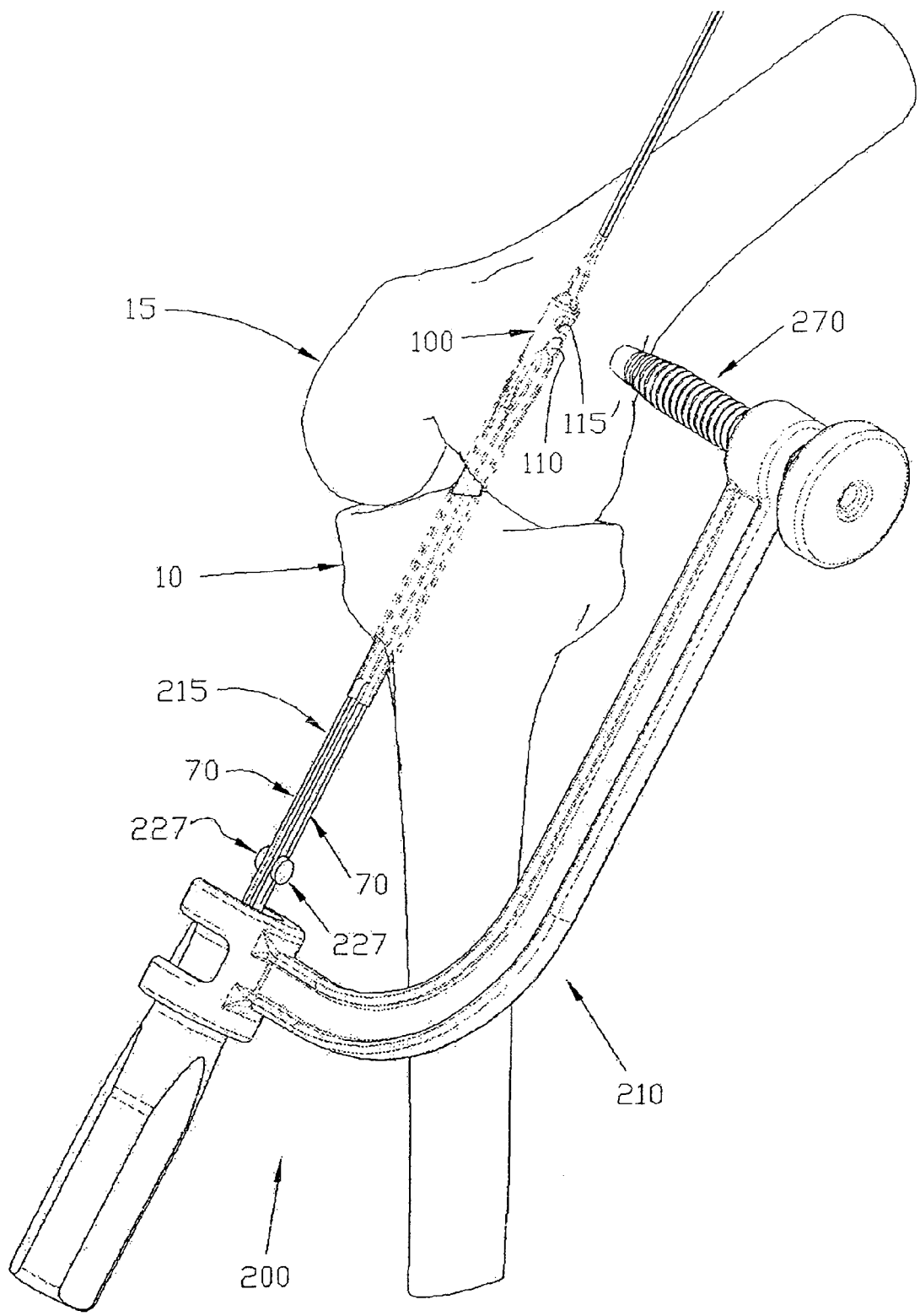
Figure 28:
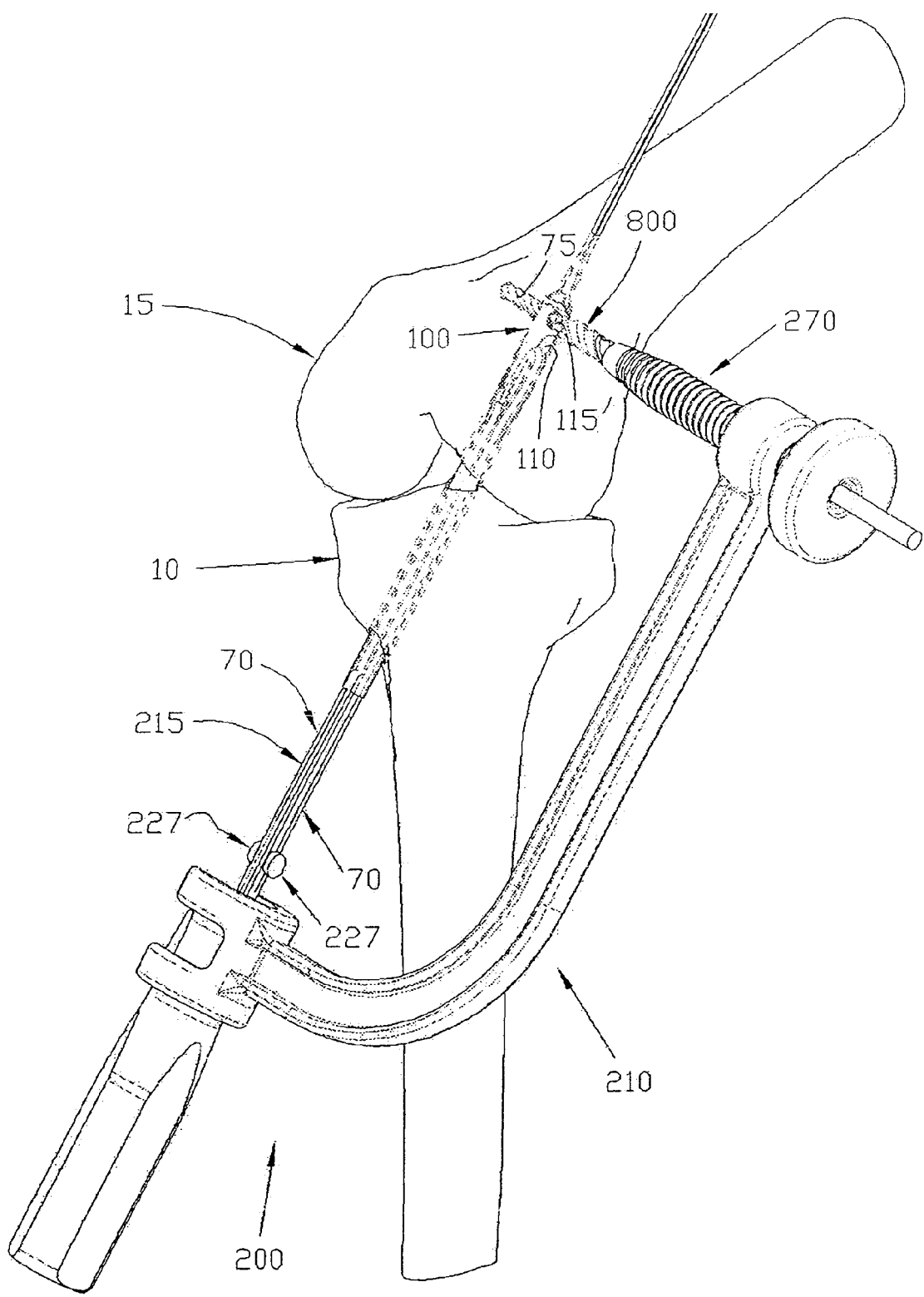

Once graft ligament support block 100 and graft ligament 35 have been advanced into position (FIG. 26), drill sleeve 270 is advanced into tight engagement with femur 15 (FIG. 27). This action will help stabilize installation tool 200 relative to femur 15. Then a transverse tunnel drill 800 (FIG. 28) is used to drill a transverse tunnel 75 through the lateral portion of femur 15, through transverse fixation pin hole 115 in graft ligament support block 100, and into the medial portion of femur 15. In this respect it will be appreciated that transverse tunnel drill 800 will be accurately and consistently directed through transverse fixation pin hole 115 in graft ligament support block 100 (FIG. 28) due to the fact that the orientation of graft ligament support block 100 and installation tool 200 (and hence drill sleeve 270) is regulated by the engagement of fingers 220 in recesses 140.

Figure 29:
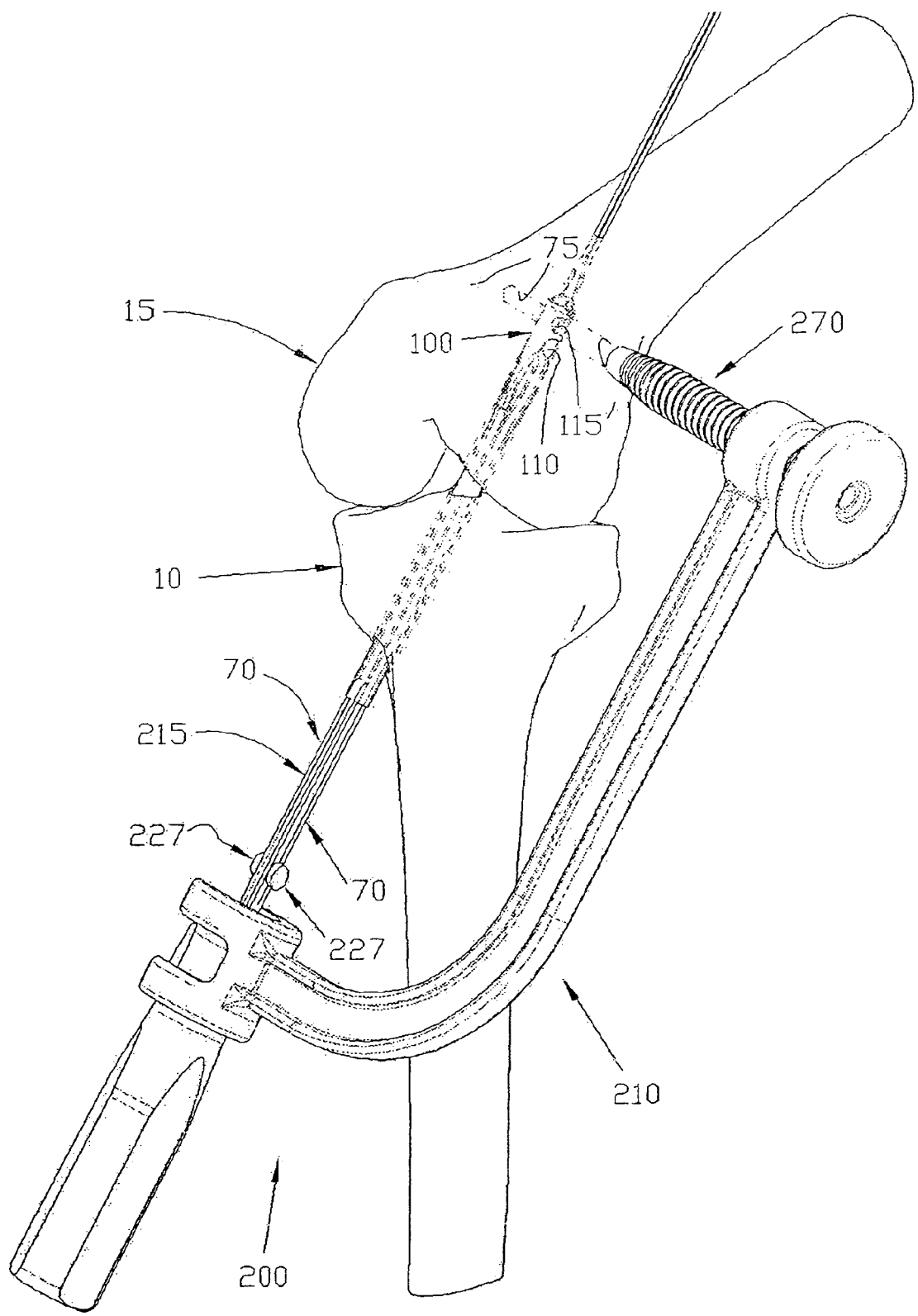
Figure 30:
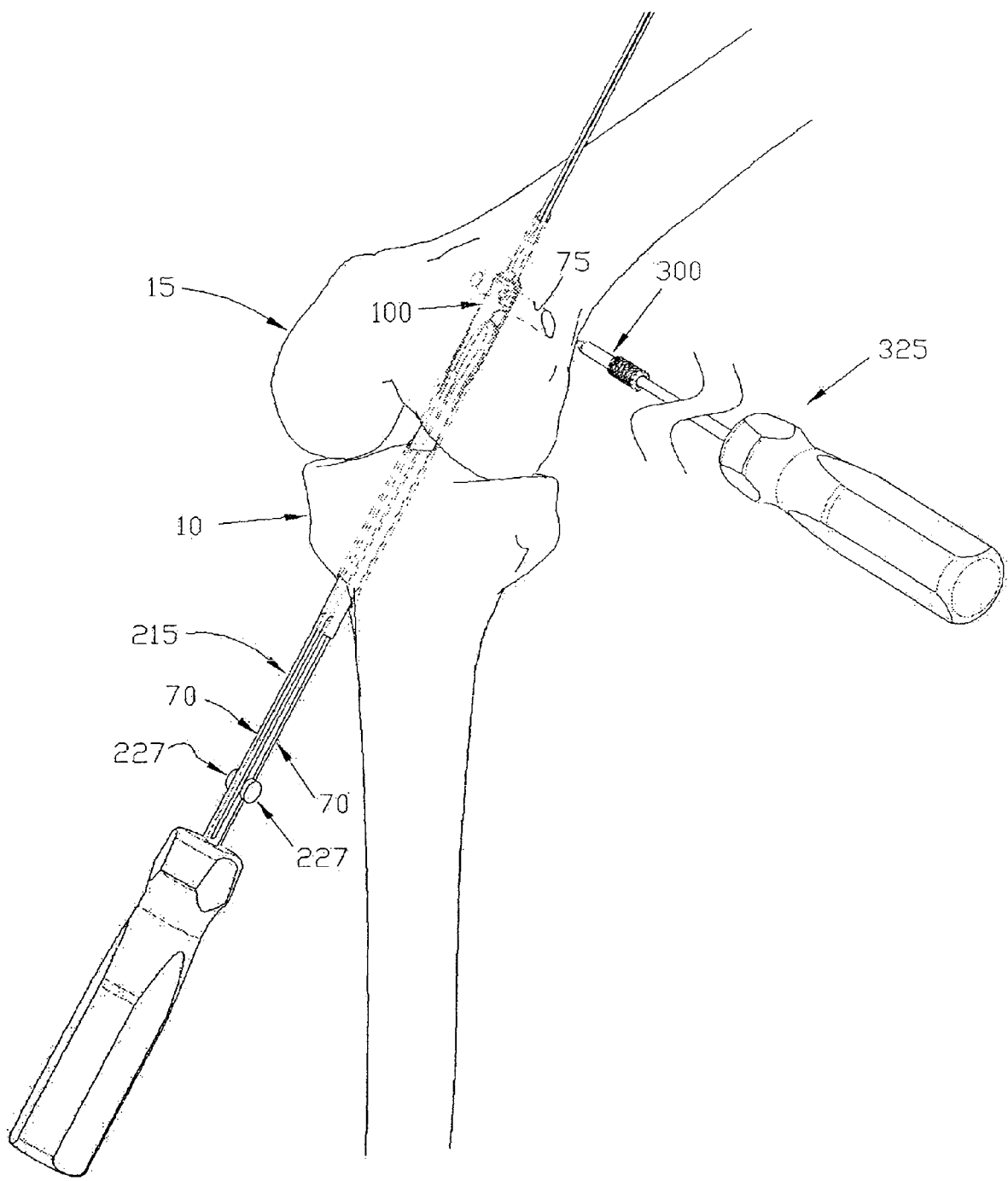
Figure 31:
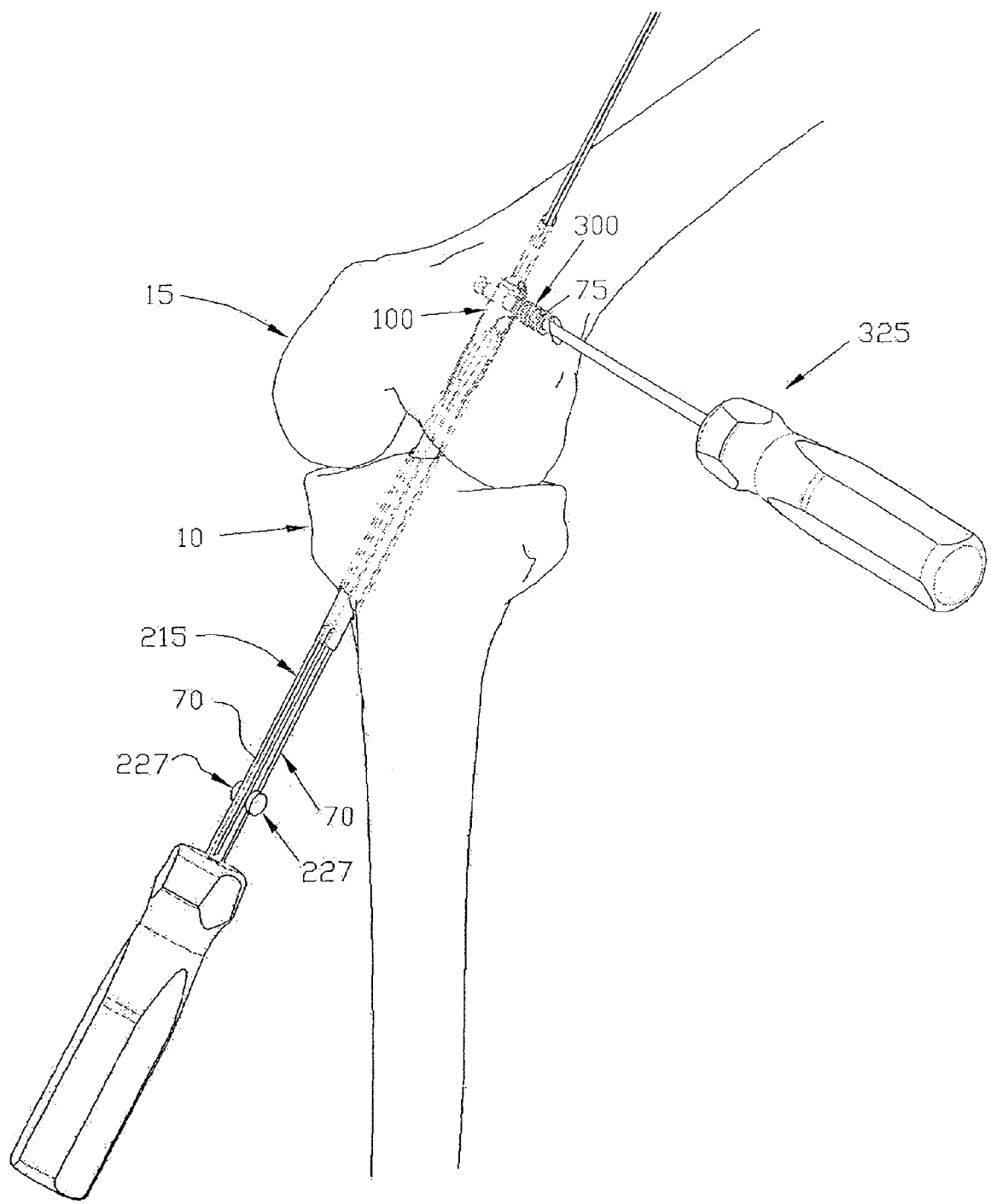
Figure 32:
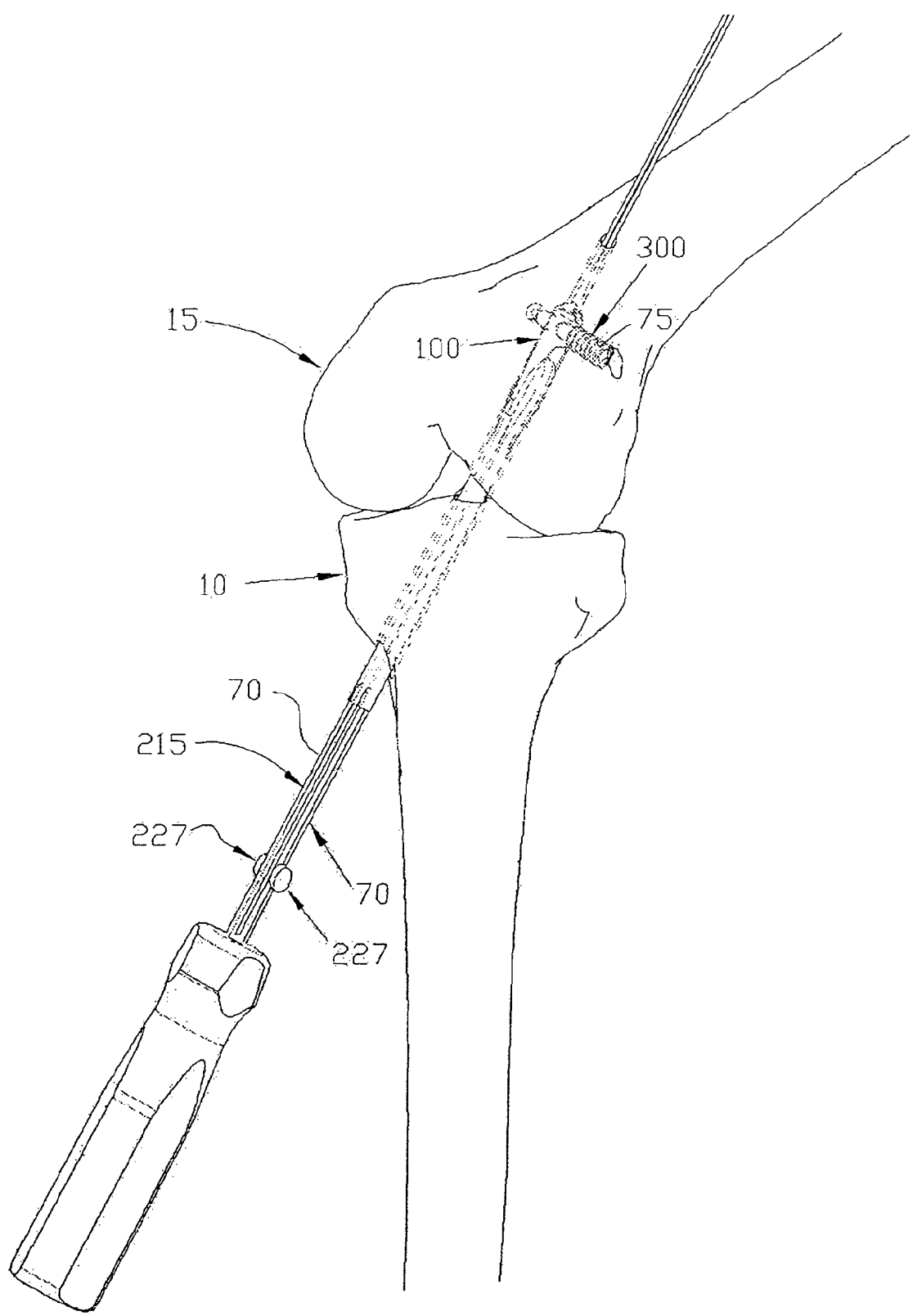
Figure 33:
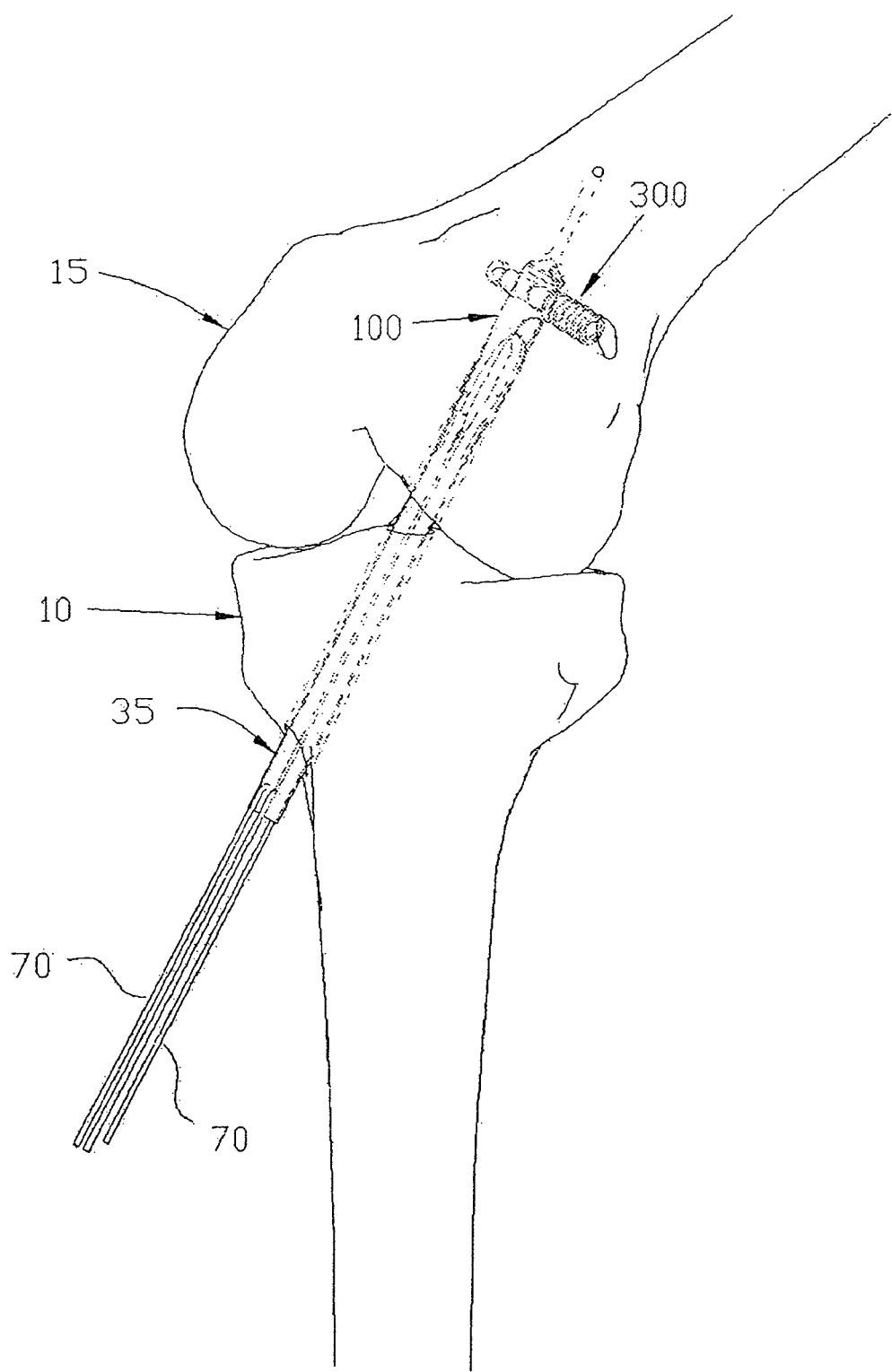

Once transverse tunnel drill 800 has been used to drill transverse tunnel 75, transverse tunnel drill 800 is removed (FIG. 29). Then drill sleeve 270 is loosened and outrigger 210 dismounted from holder 205 (FIG. 30). Then transverse fixation pin 300, mounted on a driver 325, is advanced into transverse tunnel 75 and across transverse fixation pin hole 115 in graft ligament support block 100 (FIG. 31), whereby to secure graft ligament support block 100 (and hence graft ligament 35) in femoral tunnel 25. Depending on whether section 315 of transverse fixation pin 300 is ribbed or barbed or threaded, the transverse fixation pin may be advanced by driver 325 by tapping on the proximal end of the driver with a mallet or by rotating the driver and/or both. The driver 325 is then removed (FIG. 32). Next, the two free ends of graft ligament 35 are detached from the handle's suture posts 227, and holder 205 is withdrawn (FIG. 33). In this respect it will be appreciated that graft ligament support block 100 will be held in position in femoral tunnel 25 when holder 205 is withdrawn due to the presence of transverse fixation pin 300 in transverse tunnel 75 and transverse fixation pin hole 115. Finally, the two free ends of graft ligament 35 are secured to tibia 10, thereby completing the ACL reconstruction procedure.

In the embodiment disclosed above, transverse fixation pin hole 115 (FIG. 8) is pre-formed in body 105. Such a construction is generally advantageous, since it eliminates the need to drill through body 105 after graft ligament support block 100 has been positioned in the femoral tunnel and before transverse fixation pin 300 has been passed through body 105. In addition, by pre-forming transverse fixation pin hole 115 in body 105, transverse fixation pin hole 115 can be given a desired geometry, e.g., it permits the entrance to crosspin hole 115 to be tapered, such as is shown at 155 in FIG. 8, whereby to help center transverse fixation pin 300 in transverse fixation pin hole 115. However, it should also be appreciated that, if desired, transverse fixation pin hole 115 may not be pre-formed in body 105. Instead, transverse fixation pin hole 115 may be formed in situ, at the time of surgery, e.g., by drilling across body 105 when forming transverse tunnel 75 with transverse tunnel drill 800. Where transverse fixation pin hole 115 is to be formed in situ, it is of course necessary for body 105 to be formed out of a drillable material. In addition, where transverse fixation pin hole 115 is to be formed in situ, it is preferred that body 105 be formed out of a relatively strong material, since then any misplacement (i.e., any off-center placement) of transverse fixation pin hole 115 will be well tolerated by body 105.

Figure 34:
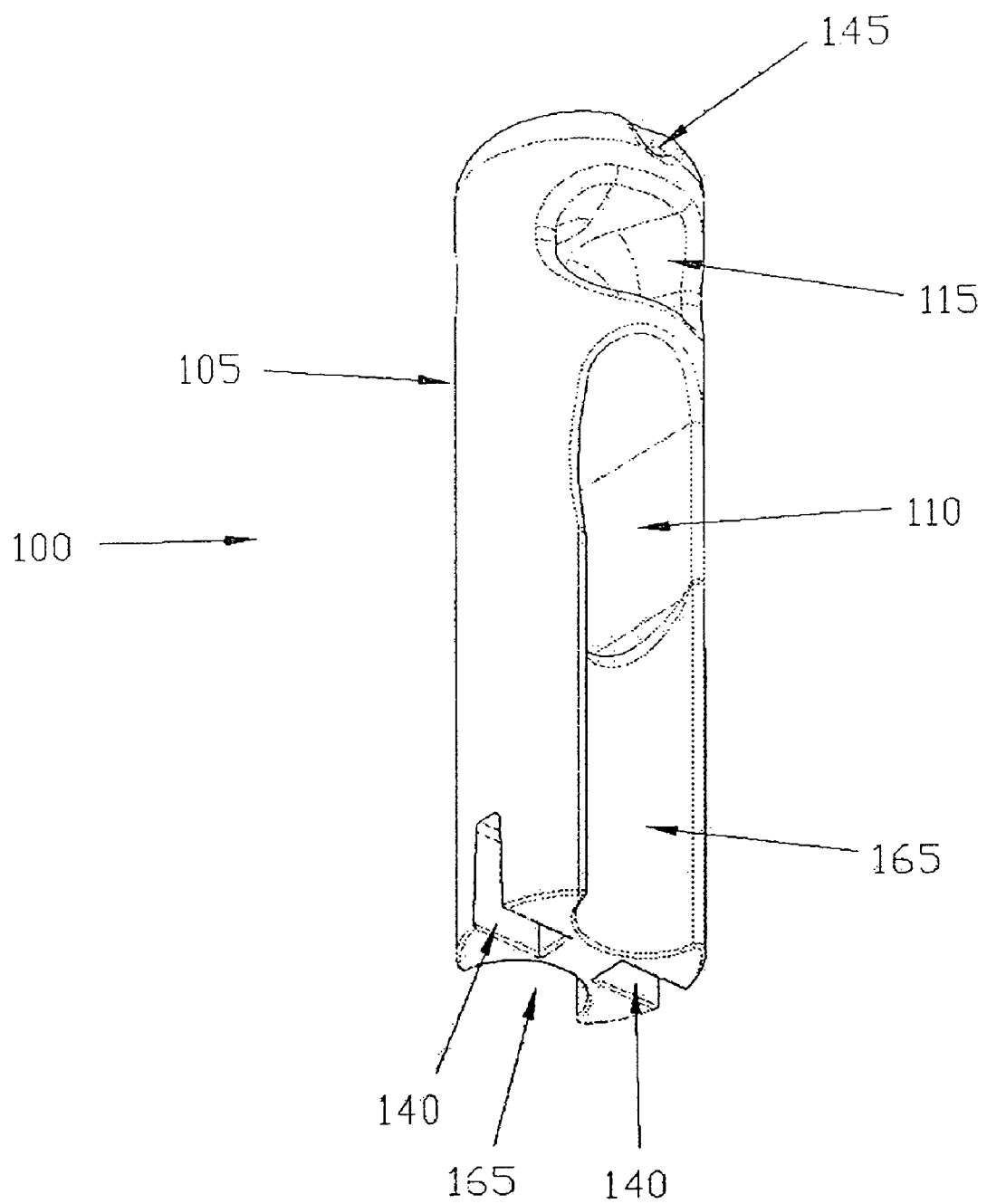
FIG. 34 is a schematic view showing another form of graft ligament support block formed in accordance with the present invention.

Additionally, in the embodiment disclosed above, the outer surface of body 105 is sculpted away proximal to graft hole 110, such as is shown at 135 in FIG. 8, so as to help accommodate the graft ligament in femoral tunnel 25. In FIG. 8, sculpting is effected so as to produce a substantially planar surface at 135. However, if desired, sculpting can be effected so as to provide alternative geometries, e.g., a surface groove, etc. Thus, for example, in FIG. 34 body 105 is shown with a pair of surface grooves 165 communicating with, and extending proximally from, graft hole 110. Surface grooves 165 are sized so as to provide a recess for seating portions of the graft ligament as the graft ligament extends proximally from graft hole 110.

Also, in the embodiment disclosed above, body 105 is shown (see, for example, FIG. 8) as having a relatively smooth outer surface. However, if desired, body 105 may have spikes or ribs, etc. formed on a side wall thereof so as to help stabilize body 105 within the bone tunnel.

Figure 35:
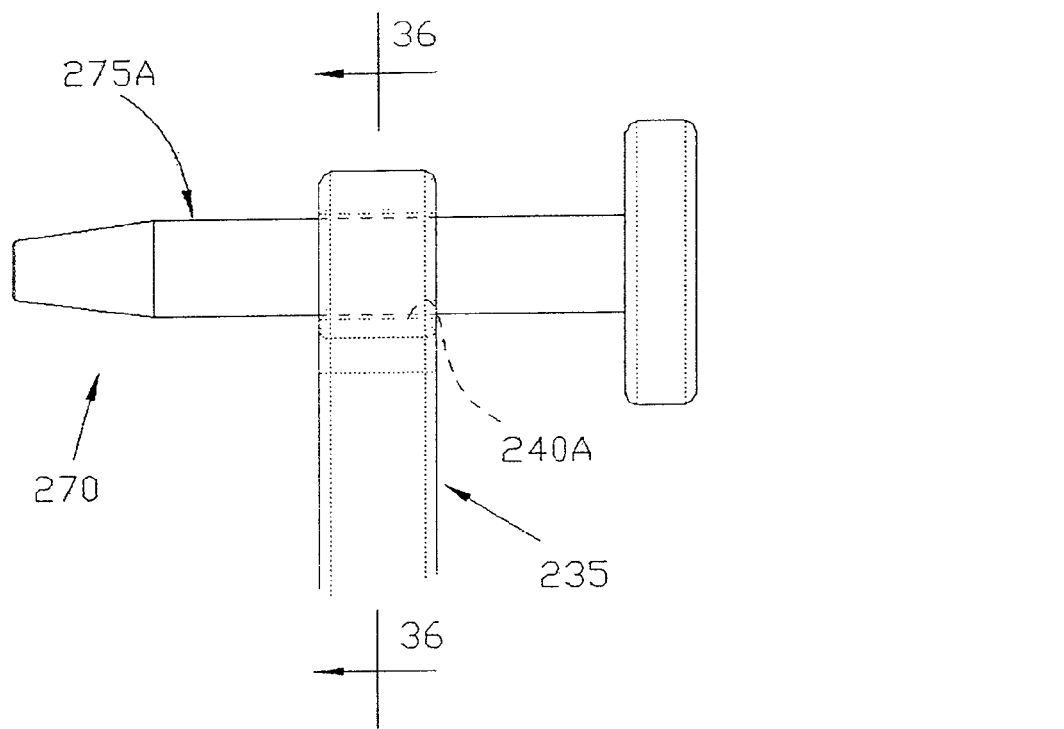
FIG. 35 is an enlarged side view showing an alternative construction for a portion of the installation tool.
Figure 36:
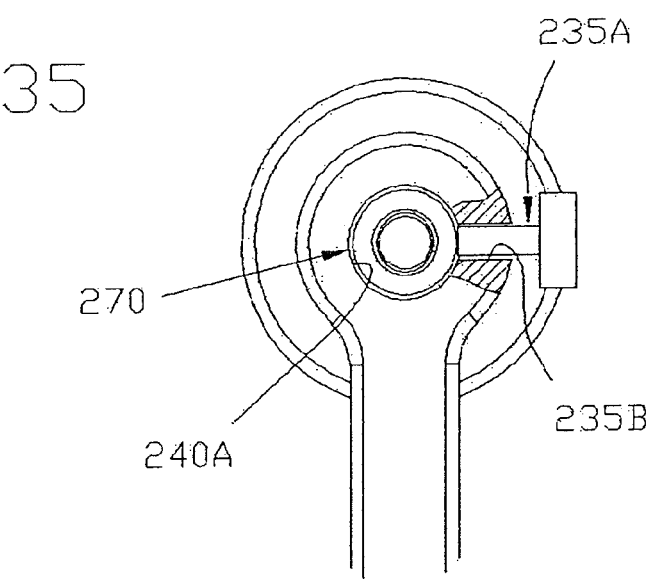
FIG. 36 is a sectional view taken along line 36-36 of FIG. 35.

Furthermore, in the embodiment disclosed above, drill sleeve 270 is movably connected to outrigger 235 via a screw connection (i.e., screw threads 275 on the exterior of drill sleeve 270 and threaded bore 240 in outrigger 235). This arrangement provides a simple and cost-effective way to movably secure drill sleeve 270 to outrigger 235. However, if desired, other types of arrangements could also be used. For example, and looking now at FIGS. 35 and 36, drill sleeve 270 could have a smooth or ribbed or roughed (e.g. knurled) exterior 275A that slides through a non-threaded bore 240A in outrigger 235, with a locking pin 235A being selectively advanceable (through a threaded bore 235B) into engagement with drill sleeve 270, whereby to selectively lock the drill sleeve to the outrigger. Still other possible arrangements for selectively locking drill sleeve 270 to outrigger 235 will be apparent to those skilled in the art of drilling and drill sleeves.

Also, in the embodiment disclosed above, drill guide 210 is shown (see, for example, FIG. 14) as being releasably secured to holder 205 via a post 255 and tightening nut 290. However, it should be appreciated that other types of connections (e.g., a "quick release" clamping mechanism) may also be used to releasably secure drill guide 210 to holder 205.

Figure 37:
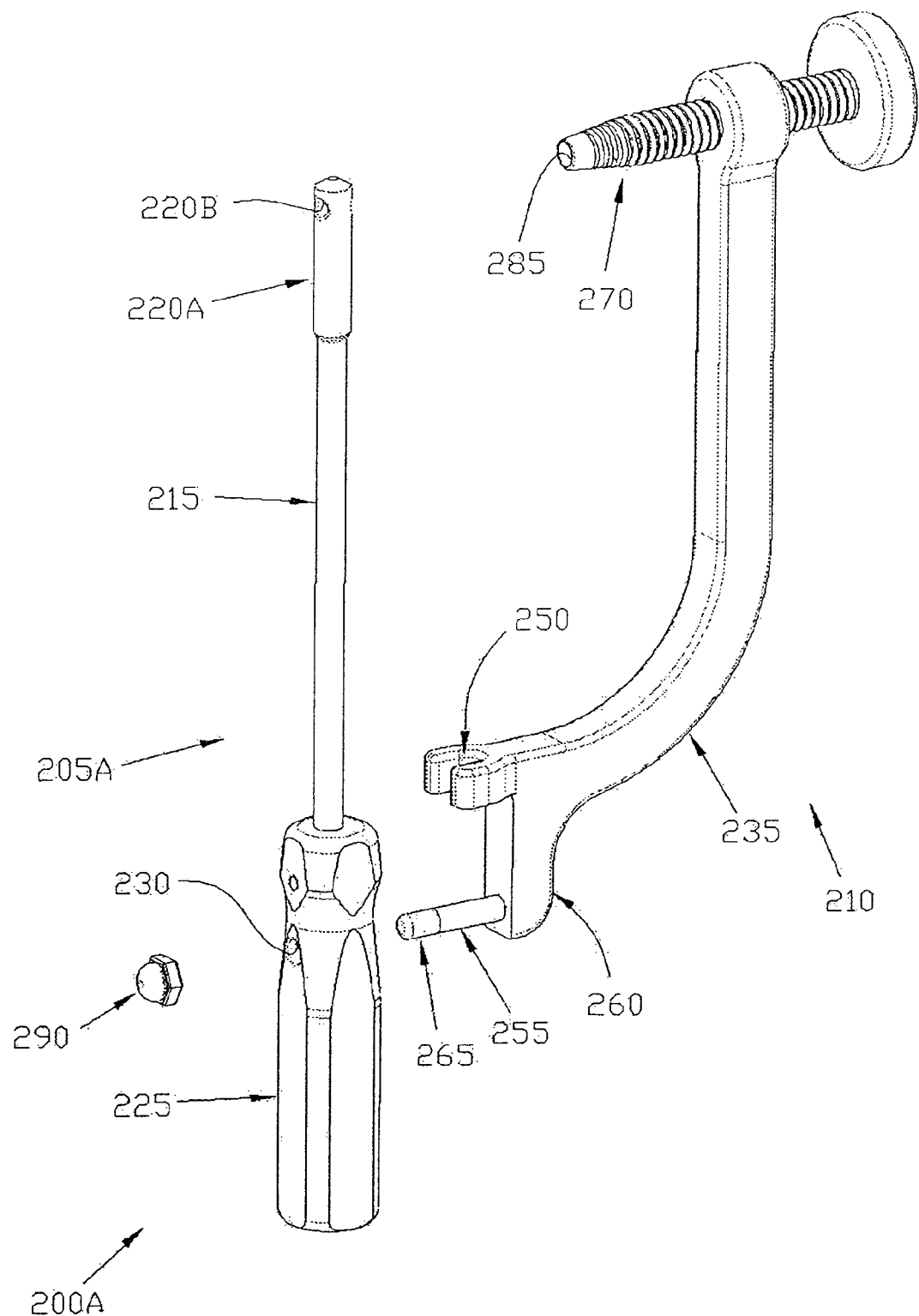
FIG. 37 is a schematic view showing a reamer drill guide formed in accordance with the present invention.
Figure 38:
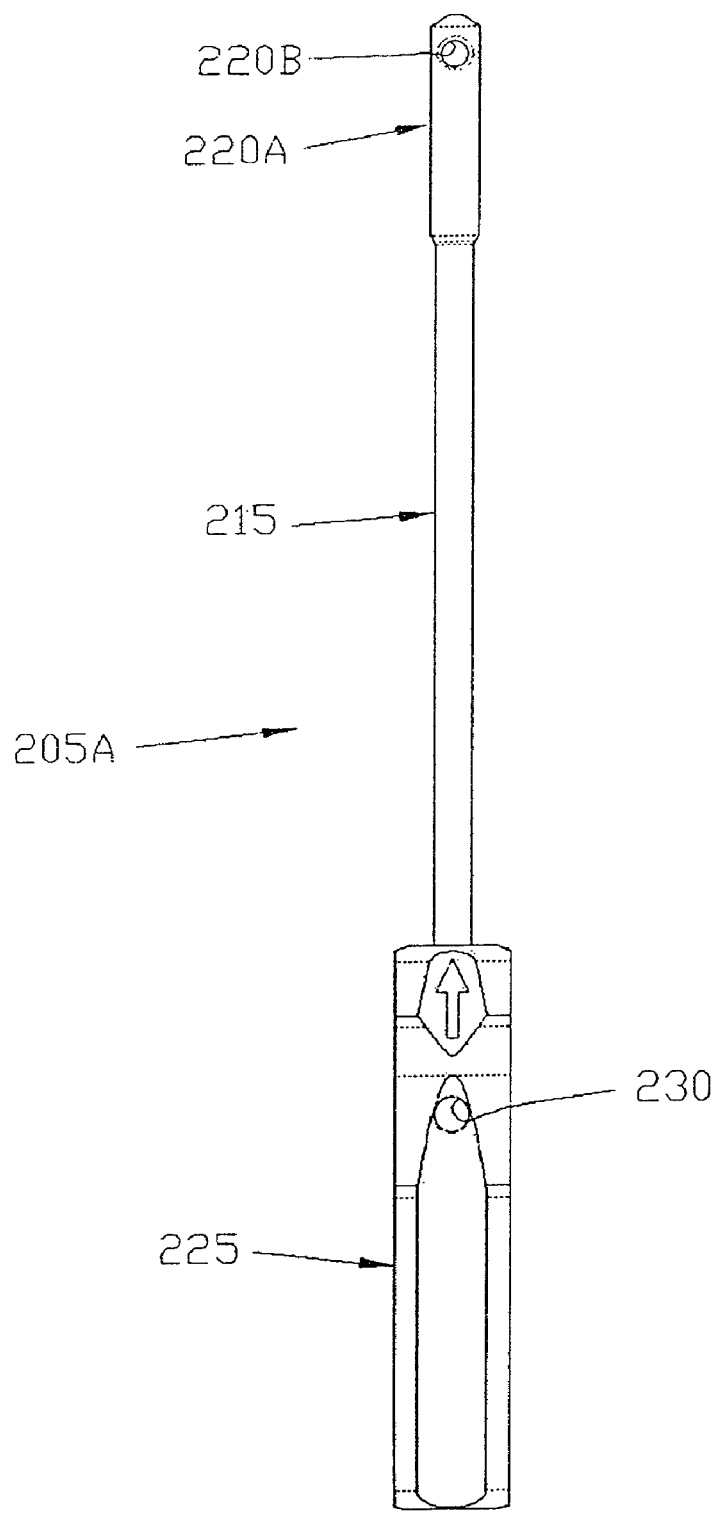
FIG. 38 is a schematic view showing the reamer element of the reamer drill guide shown in FIG. 37.

It is also possible to form transverse tunnel 75 before graft ligament support block 100 and graft ligament 35 are positioned in femoral tunnel 25. More particularly, in one possible arrangement, a reamer drill guide 200A (FIG. 37) may be used. Reamer drill guide 200A is substantially identical to the installation tool 200 described above, except as will hereinafter be described. More particularly, reamer drill guide 200A comprises a reamer 205A and the drill guide 210. Reamer 205A is substantially identical to the holder 205 described above, except that it has a cylindrical element 220A (FIGS. 37 and 38) at its distal end having a transverse hole 220B extending therethrough, and it omits the suture posts 227 which are preferably provided on holder 205. Reamer 205A is configured so that (i) its cylindrical element 220A has a diameter approximately equal to the diameter of femoral tunnel 25, and (ii) when drill guide 210 is attached to reamer 205A, the lumen 285 in drill sleeve 270 will be aligned with transverse hole 220B in reamer 205A.

Graft ligament support block 100, holder 205 and reamer drill guide 200A may be used to effect an ACL reconstruction as follows.

First, the surgical site is prepared for the graft ligament, e.g., by clearing away the damaged ACL, etc. Then a guidewire 400 (FIG. 17) is drilled up through tibia 10, across the interior of the knee joint. Preferably guidewire 400 is stopped short of engaging the bottom of femur 15 (FIG. 18). Then a cannulated tibial drill 500 (FIG. 19) is loaded onto guidewire 400 and drilled up through tibia 10 and into the interior of the knee joint (FIG. 20). Then cannulated tibial drill 500 is withdrawn back down the guidewire (FIG. 21), leaving a tibial tunnel 20.

Figure 39:
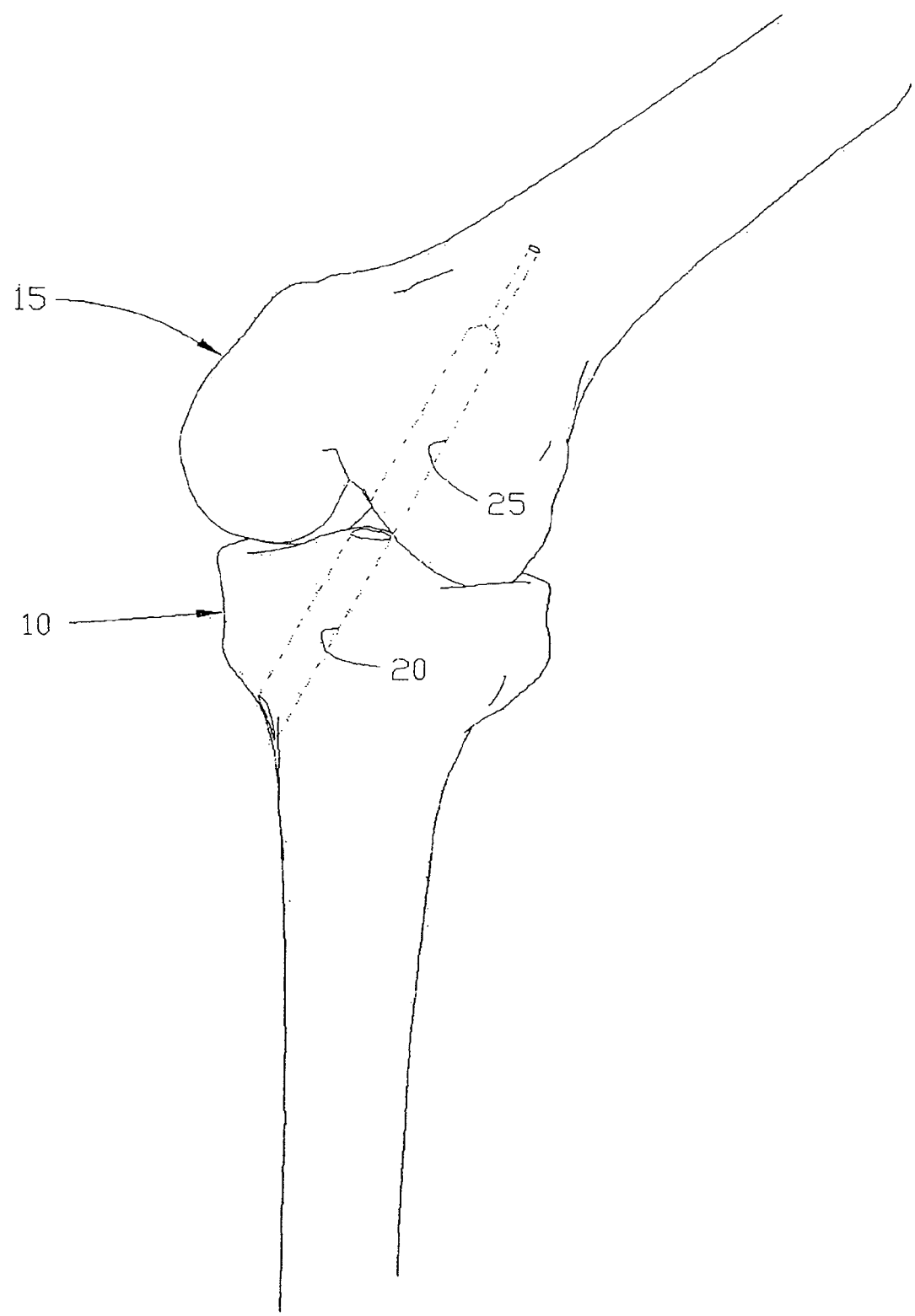
FIGS. 39-44 are a series of schematic views showing an ACL reconstruction being effected in accordance with the present invention.

Next, guidewire 400 is drilled an appropriate distance into the interior of femur 15. Then a cannulated femoral drill 600 (e.g., an acorn drill of the type shown in FIG. 22) is loaded onto guidewire 400, passed through tibial tunnel 20, across the interior of the knee joint, and then drilled up into femur 15, stopping within the interior of femur 15. Then cannulated femoral drill 600 is withdrawn back down the guidewire, leaving a femoral tunnel 25, and then guidewire 400 is withdrawn (see FIG. 39).

Next, reamer drill guide 200A is advanced so that its cylindrical element 220A is advanced through tibial tunnel 20, across the interior of the knee, and up into femoral tunnel 25. In this respect it should be appreciated that as reamer drill guide 200A is advanced through tibial tunnel 20 and femoral tunnel 25, its cylindrical element 220A will ream both bone tunnels, clearing out any intervening debris.

Figure 40:
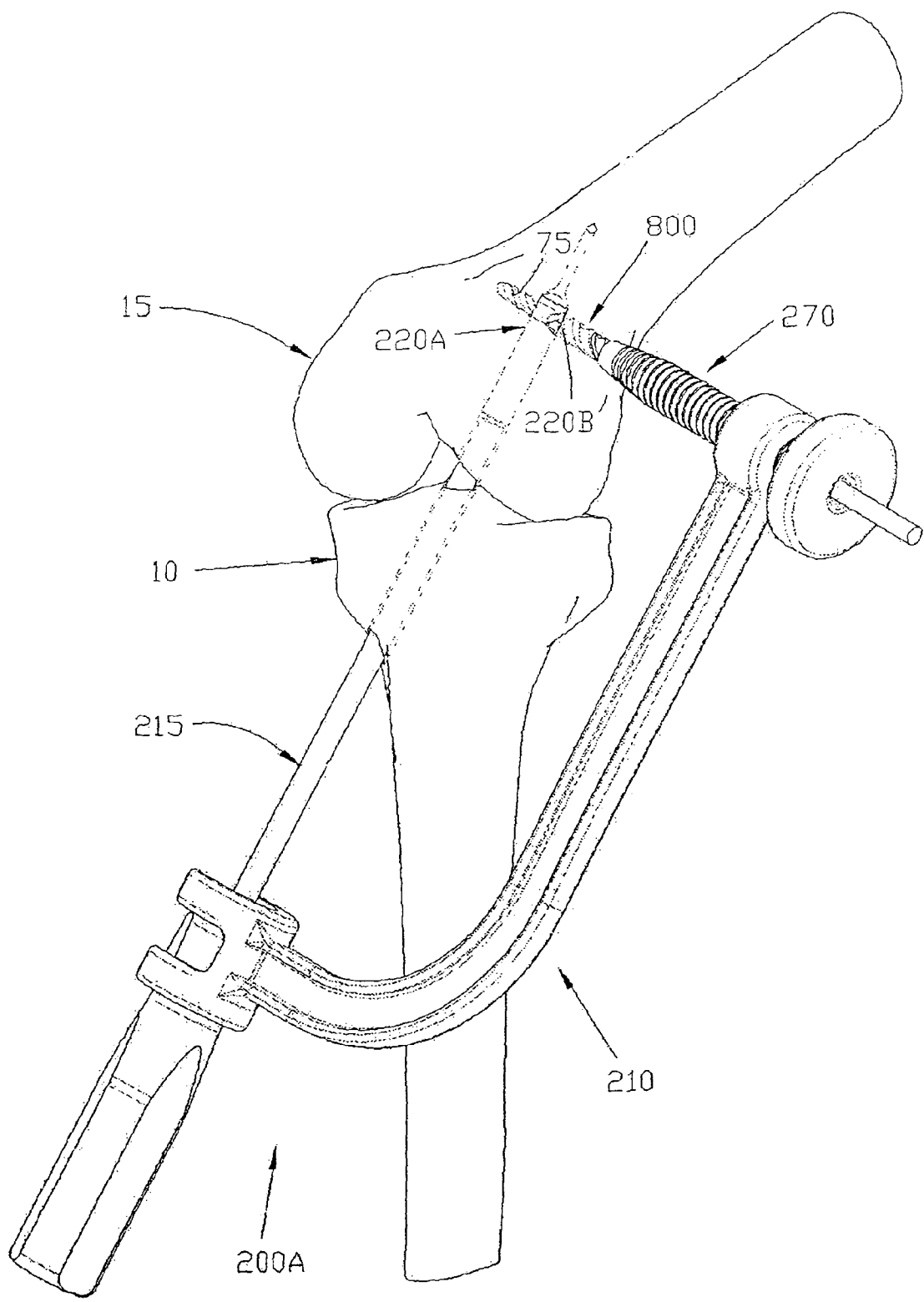

Once reamer drill guide 200A has been advanced into position, drill sleeve 270 is advanced into tight engagement with femur 15. This action will help stabilize reamer drill guide 200A relative to femur 15. Then a transverse tunnel drill 800 (FIG. 40) is used to drill a transverse tunnel 75 through the lateral portion of femur 15, through transverse hole 220B in cylindrical element 220A, and into the medial portion of femur 15. In this respect it will be appreciated that transverse tunnel drill 800 will be accurately and consistently directed through transverse hole 220B in cylindrical element 220A (FIG. 40) due to the fact that the relative orientation of cylindrical element 220A and drill sleeve 270 is regulated by the pre-defined engagement of drill guide 210 with reamer 205A.

Figure 41:
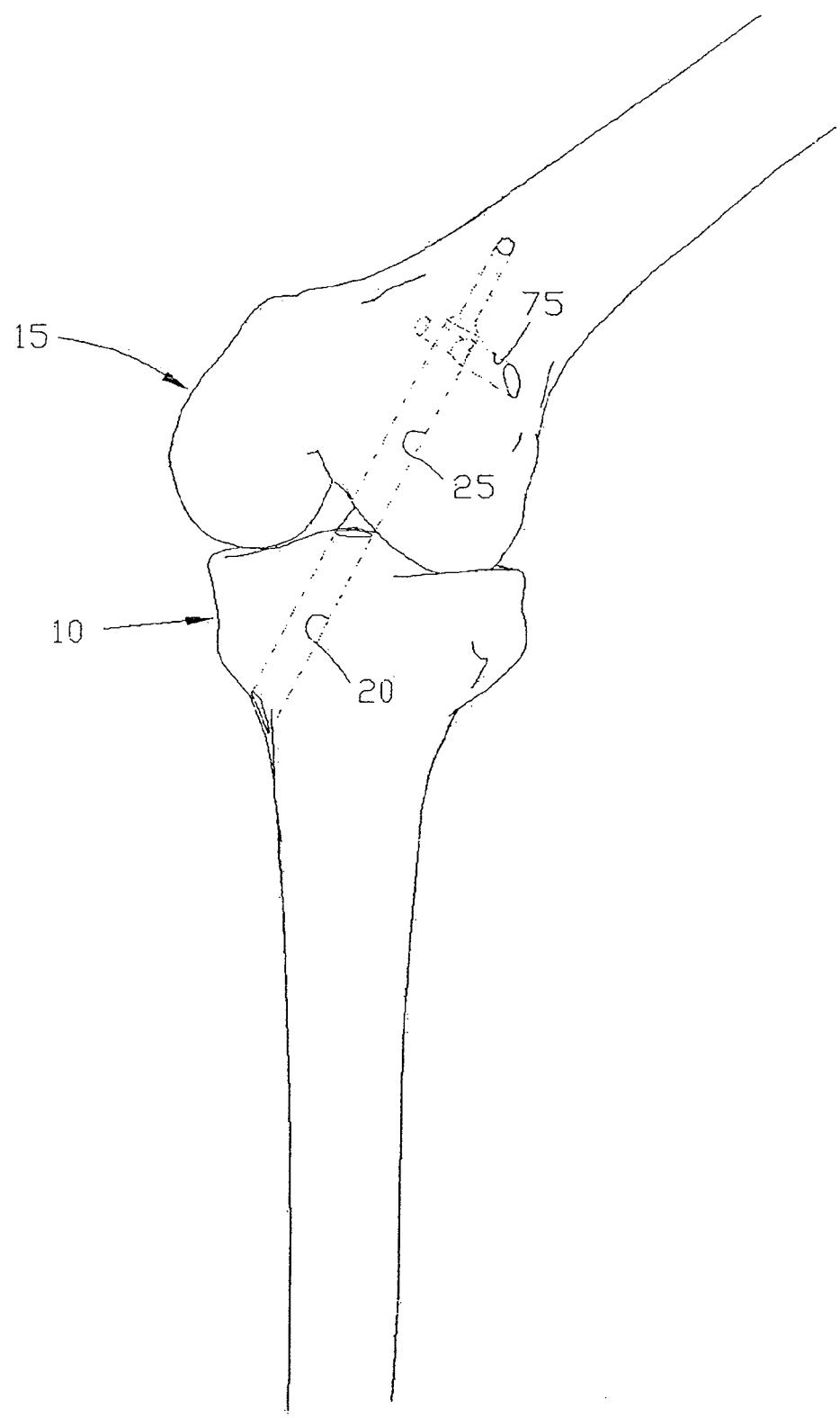

Once transverse tunnel drill 800 has been used to drill transverse tunnel 75, transverse tunnel drill 800 is removed. Then drill sleeve 270 is loosened and reamer drill guide 200A is withdrawn from the surgical site (FIG. 41).

Figure 42:
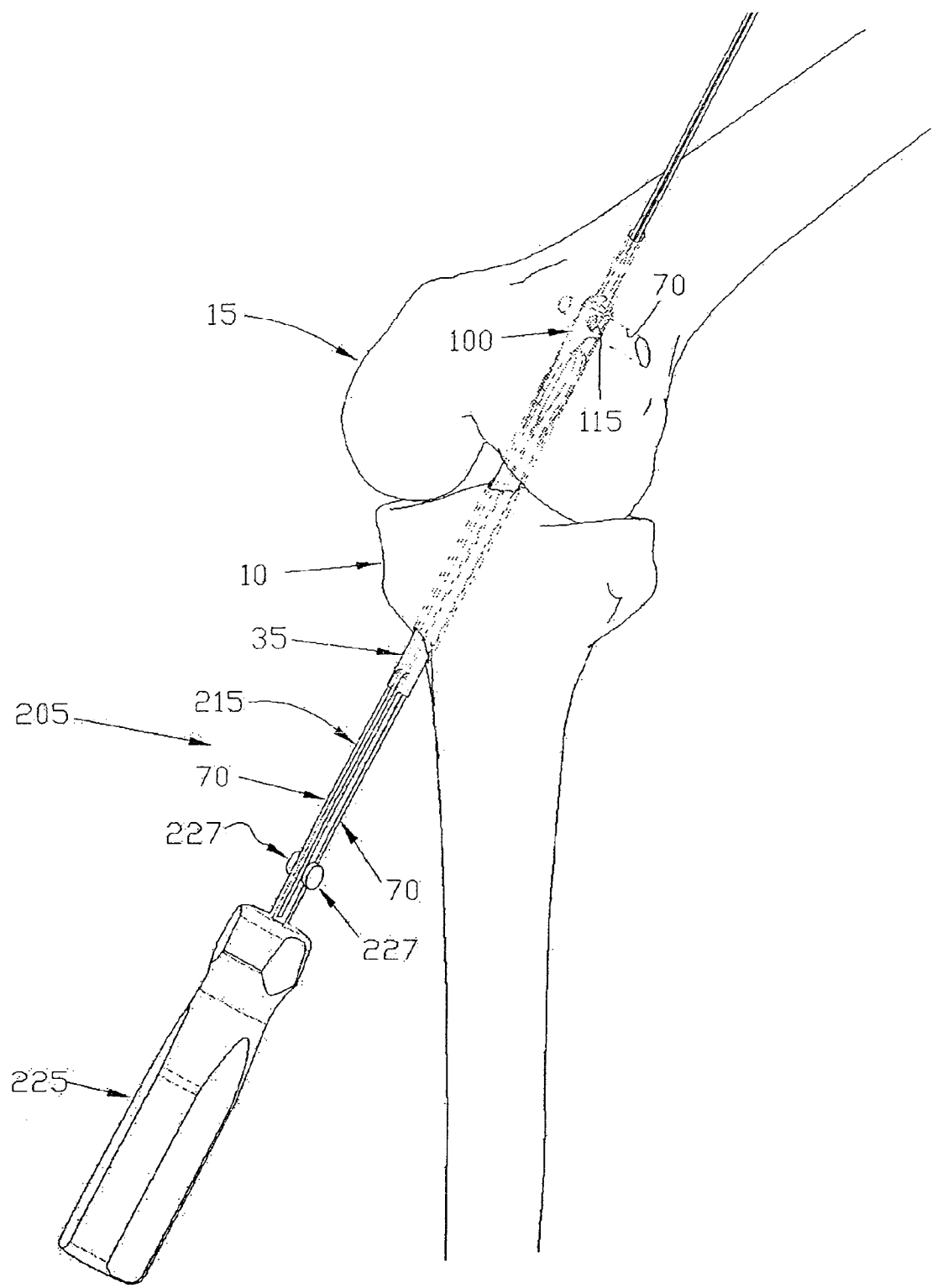
Figure 43:
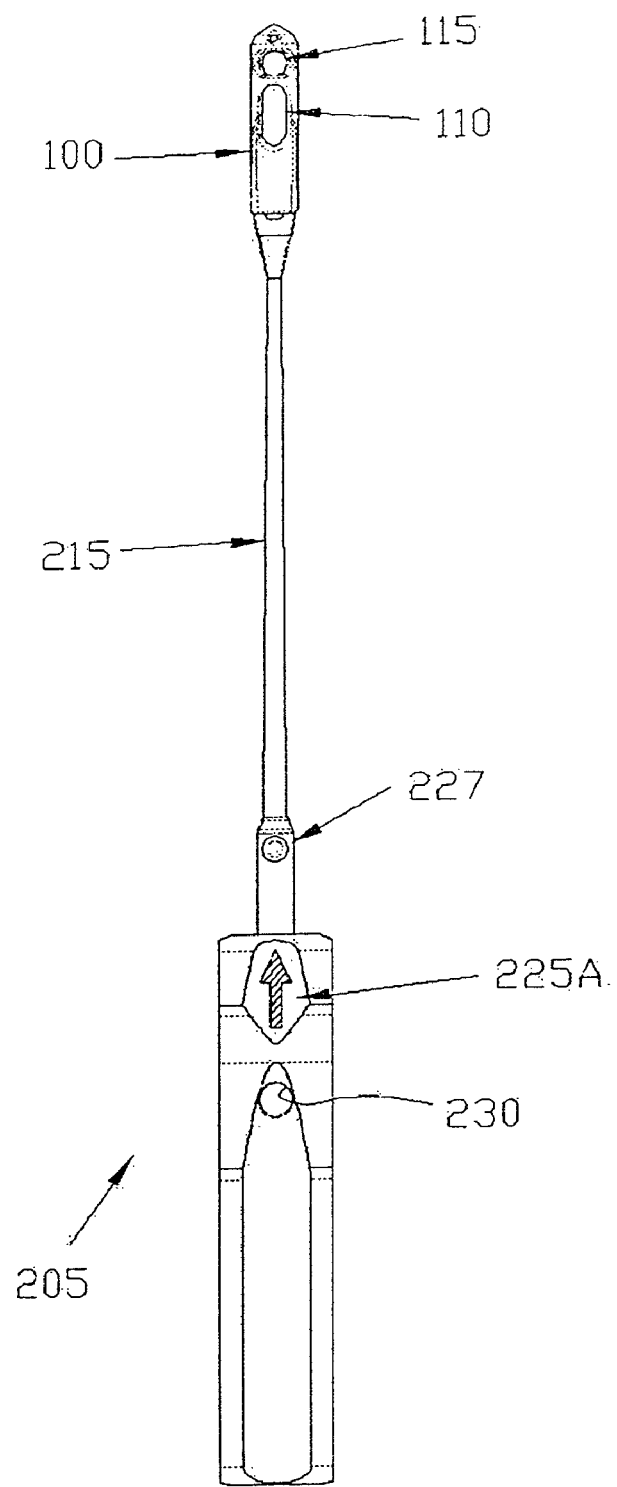

Next, a graft ligament 35 is mounted to graft ligament support block 100 by threading one end of the graft ligament through graft hole 110, and then graft ligament support block 100 is mounted to the distal end of shaft 215, i.e., by seating fingers 220 in recesses 140. The two free ends of graft ligament 35 are preferably held taut, e.g., by passing sutures 70 through the two free ends of graft ligament 35 and then securing these sutures (e.g., by winding) to suture posts 227. This arrangement will help control the two free ends of graft ligament 35 and will help hold graft ligament support block 100 to holder 205. Then holder 205 is used to push graft ligament support block 100, and hence graft ligament 35, up through tibial tunnel 20, across the interior of the knee joint, and up into femoral tunnel 25 (FIG. 42). As graft ligament support block is advanced in femoral tunnel 25, or after it has been advanced an appropriate distance into femoral tunnel 25, it is rotated as necessary, by turning handle 225 as necessary, so as to align the transverse fixation pin hole 115 with transverse tunnel 75. Such alignment may be facilitated by providing an alignment marker (e.g., such as the alignment marker 225A shown in FIG. 43) on handle 225.

Figure 44:
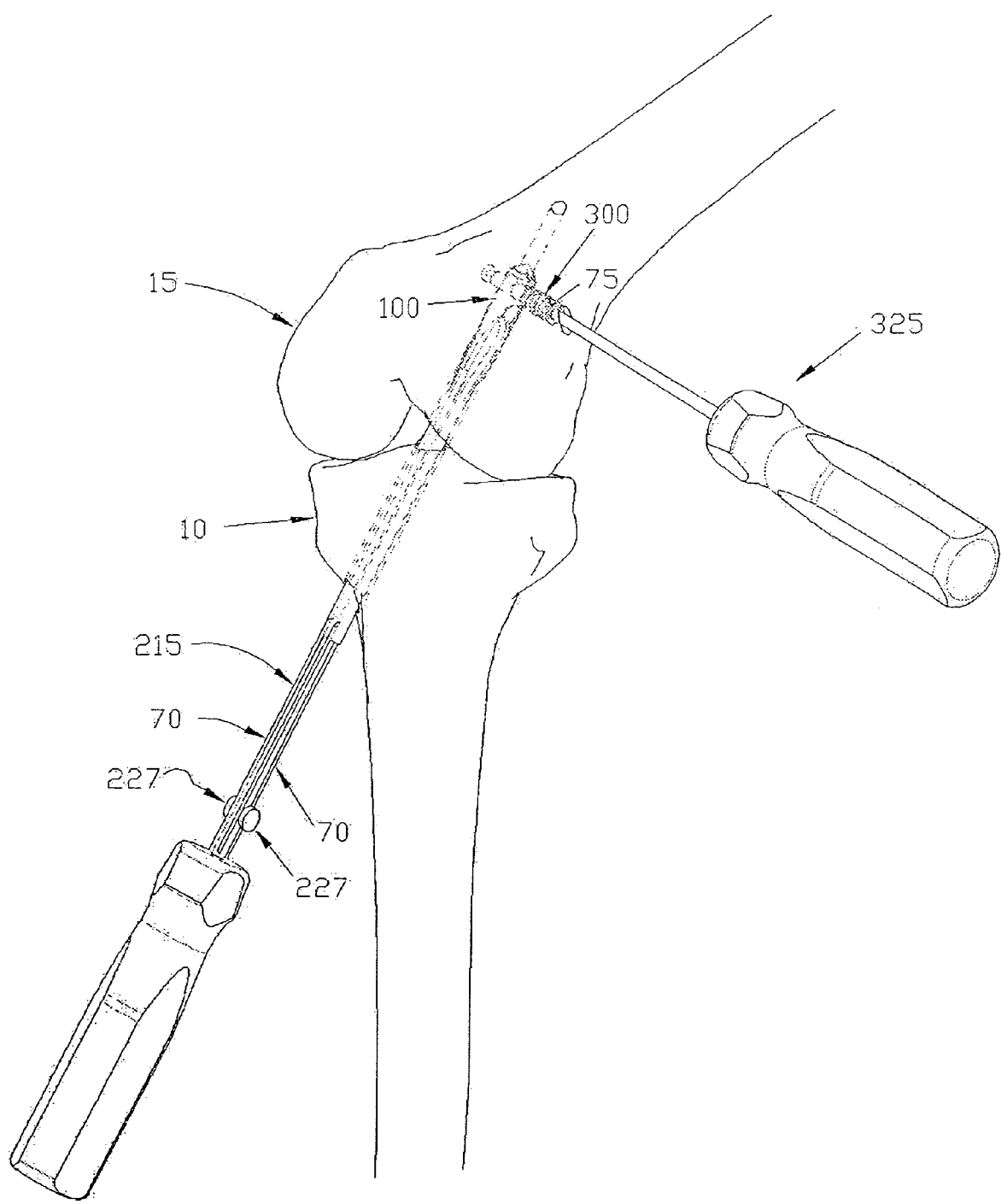

Then transverse fixation pin 300, mounted on a driver 325, is advanced into transverse tunnel 75 and across transverse fixation pin hole 115 in graft ligament support block 100 (FIG. 44), whereby to secure graft ligament support block 100 (and hence graft ligament 35) in femoral tunnel 25. Then driver 325 is removed. Next, the two free ends of graft ligament 35 are detached from the handle's suture posts 227, and holder 205 is withdrawn. In this respect it will be appreciated that graft ligament support block 100 will be held in position in femoral tunnel 25 when holder 205 is withdrawn due to the presence of transverse fixation pin 300 in transverse tunnel 75 and transverse fixation pin hole 115. Finally, the two free ends of graft ligament 35 then secured to tibia 10, thereby completing the ACL reconstruction procedure.

In the preceding discussion, the present invention has been discussed on the context of an ACL reconstruction. However, it should also be appreciated that the present invention may also be used in connection with the other types of ligament reconstructions and/or other types of anatomical reconstructions.

What is claimed:

1. A system for installation of a graft ligament support block, the system comprising:
    an installation tool comprising:
        a holder including a shaft having a handle at a proximal end and a distal end configured for selectively engaging the graft ligament support block; and
        a drill guide including an outrigger having a bore formed on its distal end for selectively receiving a drill sleeve, wherein a proximal end of the drill guide includes a post for selectively engaging the holder.

2. The system according to claim 1, wherein the distal end of the holder includes a pair of fingers.

3. The system according to claim 1, wherein an end of the post is threaded to receive a nut.

4. The system according to claim 3, wherein the handle includes a post hole for selectively receiving the post of the drill guide.

5. The system according to claim 1, wherein the bore formed in the outrigger is threaded.

6. The system according to claim 5, further including a drill sleeve.

7. The system according to claim 6, wherein the drill sleeve includes threads along a length thereof.

8. The system according to claim 7, wherein the drill sleeve terminates in a proximal head.

9. The system according to claim 1, further including one or more drills.

10. The system according to claim 9, wherein at least one of the one or more drills is cannulated.

11. The system according to claim 10, wherein a first cannulated drill is configured to form a tibial tunnel.

12. The system according to claim 11, wherein a second cannulated drill is configured to form a femoral tunnel.

13. The system according to claim 9, including a first drill for forming a tibial tunnel, a second drill for forming a femoral tunnel and a third drill for forming a transverse tunnel.

14. The system according to claim 9, further including a guidewire configured to be received through the at least one cannulated drill.

15. The system according to claim 1, wherein the shall is configured for reception through a tibial tunnel, across a knee joint and into a femoral tunnel.

16. A system for installation of a graft ligament support block, the system comprising:
    an installation tool comprising:
        a holder including a shaft having a handle at a proximal end and a distal end configured for selectively engaging the graft ligament support block;
        a drill guide including an outrigger having a bore formed on its distal end for selectively receiving a drill sleeve and a proximal end configured to selectively engage the holder; and
        a reamer guide configured for selective engagement with the proximal end of the drill guide.

* * * * *